United States Patent
Haakenson, Jr. et al.

(10) Patent No.: US 10,398,144 B2
(45) Date of Patent: *Sep. 3, 2019

(54) N-,C-DISUBSTITUTED AZOLES AND COMPOSITIONS AND METHODS FOR CONTROLLING NEMATODE PESTS

(71) Applicant: Monsanto Technology LLC, St. Louis, MO (US)

(72) Inventors: William P. Haakenson, Jr., St. Louis, MO (US); Urszula J. Slomczynska, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/669,006

(22) Filed: Aug. 4, 2017

(65) Prior Publication Data

US 2017/0332639 A1  Nov. 23, 2017

Related U.S. Application Data

(60) Continuation of application No. 15/195,331, filed on Jun. 28, 2016, now Pat. No. 9,763,449, which is a division of application No. 14/865,000, filed on Sep. 25, 2015, now Pat. No. 9,402,397, which is a division of application No. 14/210,917, filed on Mar. 14, 2014, now Pat. No. 9,173,401.

(60) Provisional application No. 61/787,971, filed on Mar. 15, 2013.

(51) Int. Cl.

| | |
|---|---|
| *A01N 43/647* | (2006.01) |
| *C07D 407/04* | (2006.01) |
| *A01N 43/56* | (2006.01) |
| *A01N 25/00* | (2006.01) |
| *A01N 43/50* | (2006.01) |
| *A01N 25/34* | (2006.01) |
| *C07D 409/04* | (2006.01) |
| *C07D 405/04* | (2006.01) |

(52) U.S. Cl.
CPC .......... *A01N 43/647* (2013.01); *A01N 25/00* (2013.01); *A01N 25/34* (2013.01); *A01N 43/50* (2013.01); *A01N 43/56* (2013.01); *C07D 405/04* (2013.01); *C07D 407/04* (2013.01); *C07D 409/04* (2013.01)

(58) Field of Classification Search
None
See application file for complete search history.

(56) References Cited

U.S. PATENT DOCUMENTS

| | | |
|---|---|---|
| 3,509,153 A | 4/1970 | Shin et al. |
| 4,465,017 A | 8/1984 | Simmons |
| 4,759,945 A | 7/1988 | Nemecek et al. |
| 4,791,124 A | 12/1988 | Lutomski et al. |
| 4,839,349 A | 6/1989 | Covey et al. |
| 4,908,357 A | 3/1990 | Lutomski |
| 5,080,925 A | 1/1992 | Kouno |
| 5,107,787 A | 4/1992 | Kouno |
| 5,389,399 A | 2/1995 | Bazin et al. |
| 5,393,767 A | 2/1995 | Dick |
| 5,554,445 A | 9/1996 | Struszczyk et al. |
| 5,891,246 A | 4/1999 | Lund |
| 5,918,413 A | 7/1999 | Otani et al. |
| 6,048,714 A | 4/2000 | Hiromoto |
| 6,069,157 A | 5/2000 | Banks |
| 6,310,049 B1 | 10/2001 | Wada et al. |
| 7,230,116 B2 | 6/2007 | Fischer et al. |
| 9,226,505 B2 | 1/2016 | Müller et al. |
| 9,402,397 B2 | 1/2016 | Slomczynska et al. |
| 2002/0013326 A1 | 1/2002 | Tiebes et al. |
| 2003/0162812 A1 | 8/2003 | Harmsen et al. |
| 2004/0186295 A1 | 9/2004 | Cosford et al. |
| 2004/0209776 A1 | 10/2004 | Farooq et al. |
| 2004/0220199 A1 | 11/2004 | Asrar et al. |
| 2004/0242664 A1 | 12/2004 | Fischer et al. |
| 2007/0135506 A1 | 6/2007 | Zeun et al. |
| 2007/0203101 A1 | 8/2007 | Fischer et al. |
| 2007/0259862 A1 | 11/2007 | Wallberg et al. |
| 2008/0293573 A1 | 11/2008 | Fischer et al. |
| 2010/0062942 A1 | 3/2010 | Fischer et al. |
| 2010/0267714 A1 | 10/2010 | Jorgensen et al. |
| 2011/0143942 A1 | 6/2011 | Fischer et al. |
| 2013/0067620 A1 | 3/2013 | Bradley et al. |
| 2014/0329684 A1 | 11/2014 | Müller et al. |
| 2015/0368295 A1 | 12/2015 | Taran et al. |
| 2016/0007605 A1 | 1/2016 | Slomczynska et al. |

FOREIGN PATENT DOCUMENTS

| | | |
|---|---|---|
| DE | 19923317 A1 | 11/2000 |
| EP | 0339854 B1 | 5/1993 |
| EP | 0846686 A1 | 6/1998 |

(Continued)

OTHER PUBLICATIONS

CAPLUS printout of "Latif et al., Carbonyl and Thiocarbonyl compounds. Part XVIII. Newer polyhalo-1,3-benzodioxoles and carbamates incorporating methylenedioxyphenyl structure. Indian Journal of Chemistry, Section B: Organic Chemistry Including Medicinal Chemistry, 1980, 19B(11), 975-979."*

CAPLUS printout of "Robev, Stefan K. Synthesis of triazoles and oxadiazoles from 2-aryl-3-phenyl-4-imno-5-cyano-3,4-dihydropyrimidines. Tetrahedron Letters, 1982, 23, 2903-2906."*

Gupton et al., The application of vinylogous iminium salt derivatives to the regiocontrolled preparation of heterocyclic appended pyrazoles. Tetrahedron, 2002, 58, 5467-5474.*

Machida, M., et al., "Photocycloaddition of arylcarbothioamides with unsaturated systems. Synthesis of 3, 5-diarl-1, 2, 4-thiadiazoles and 3-aryl-4, 4, 5, 5-tetramethylisothiazolines via photogenerated nitrile sulfides", Tetrahedron Letters, 1984, 25(4):409-410, 2 pages.

(Continued)

*Primary Examiner* — Po-Chih Chen

(74) *Attorney, Agent, or Firm* — Stinson LLP; Lawrence M. Lavin, Jr.

(57) ABSTRACT

Provided herein are new N-,C-disubstituted azoles and derivatives thereof that exhibit nematicidal activity and are useful, for example, in methods for the control of unwanted nematodes.

8 Claims, No Drawings

(56) References Cited

FOREIGN PATENT DOCUMENTS

| EP | 1970375 A1 | 9/2008 |
|---|---|---|
| JP | 2007051243 A | 3/2007 |
| JP | 2009267176 A | 11/2009 |
| WO | 87006429 A1 | 11/1987 |
| WO | 0107413 A1 | 2/2001 |
| WO | 02076983 A1 | 10/2002 |
| WO | 02100826 A2 | 12/2002 |
| WO | 03018008 A1 | 3/2003 |
| WO | 2003029210 A2 | 4/2003 |
| WO | 03106436 A1 | 12/2003 |
| WO | 2004110351 A2 | 12/2004 |
| WO | 2005023773 A1 | 3/2005 |
| WO | 2006084338 A1 | 8/2006 |
| WO | 2006097030 A1 | 9/2006 |
| WO | 2007039782 A1 | 4/2007 |
| WO | 2007042544 A2 | 4/2007 |
| WO | 2007103456 A2 | 9/2007 |
| WO | 2007130820 A2 | 11/2007 |
| WO | 2007130822 A2 | 11/2007 |
| WO | 2007149395 A2 | 12/2007 |
| WO | 2008049864 A1 | 5/2008 |
| WO | 2008057254 A2 | 5/2008 |
| WO | 2008085008 A1 | 7/2008 |
| WO | 2009023721 A1 | 2/2009 |
| WO | 2009102736 A1 | 8/2009 |
| WO | 2010070068 A2 | 6/2010 |
| WO | 2010093650 A2 | 8/2010 |
| WO | 2012030887 A1 | 3/2012 |
| WO | 2014008257 A3 | 2/2014 |
| WO | 2014089219 A1 | 6/2014 |

OTHER PUBLICATIONS

Meegalla, S. K., et al., "Synthesis and GABA Receptor Potency of 3-thiomethyl-4-(hetero)aryl-5-amino-1-phenylpyrazoles," Bioorganic & Medicinal Chemistry Letters, 2004, 14:4949-4953, XP027213203.
Mojtahedi, M. M., et al., "Convenient Ultrasound Mediated Synthesis of Substituted Pyrazolones Under Solvent-Free Conditions," Ultrasonics Sonochemistry, 2008, 15:828-832, XP022594113.
Reinov, M. V., et al., "Heterocyclic Derivatives of Fullerene C60. 1. Synthesis of New Fulleropyrazolines by the 1,3-Dipolar Cycloaddition of Nitrile Imines", Chemistry of Heterocyclic Compounds, 2004, 40(2):188-193, 7 pages.
Wentrup, C., et al., "Nitrile Imine and Carbene Rearrangements. From Furfural to Benzofulvene-8-carboxaldehyde, 8-Benzofulvenylcarbene, and 1-Vinylideneindene", J. Org. Chem., 1980, 45(8):1407-1409, 3 pages.
Andersen, J., et al., "Rapid Synthesis of Aryl Azides from Aryl Halides Under Mild Conditions," 2005, Synlett, 14:2209-2213.
Atkins, J.M., et al., A two-stage iterative process for the synthesis of poly-oxazoles, Organic Letters, 2005, 7/2:3351-3354.
Barker, K.R., et al. "Plant and Soil Nematodes: Societal Impact and Focus for the Future," 1994, J Nematology, 26/2: 127-137.
Becker, H., "Seeking New Controls for Costly Nematodes," 1999, Agricultural Research Magazine, 47/3:22-24.
CAS Registry No. 678167-41-4; STN Entry Date Apr. 30, 2004, 2-(2-chlorophenyl)-5-(2-methyl-3-furanyl )-1,3,4-Oxadiazole.
Carpenter, J., et al., "Township Limits on 1,3-D Will Impact Adjustment to Methyl Bromide Phase-Out," 2001, California Agriculture, 55/3:12-18.
Carter, C., "Costs Uncertain: Methyl Bromide Phase-Out Becomes Reality," 2001, California Agriculture, 55/3:2.
Cesarini, S., et al.,"1,3,4-Oxadiazole Formation as Traceless Release in Solid Phase Organic Synthesis," 2006, Tetrahedron, 62/43:10223-10236.
Crow, W.T., "Alternatives to Fenamiphos for Management of Plant-Parasitic Nematodes on Bermudagrass," 2005, Journal of Nematology, 37/4/:477-482.
Davydov, D.V., et al., "Regioselective Arlyation of N-Tributylstannylated 5-Substituted Tetrazoles by Diaryliodonium Salts in the Presence of Cu(OAc)2," 2002, Tetrahedron Letters, Elsevier, Amsterdam, NL, 43/35:6217-6219, XP027241945.
Duval, R., et al., "Rapid Discovery of TriazolobenzylideneThiazolopyrimidines (TBTP) as CDC25 Phosphatase Inhibitors by Parallel Click Chemistry and in Situ Screening," 2009, J. Combin Chem, 11/6:947-950, 4 pages.
Enders, C., et al., "End-Group Telechelic Oligo- and Polythiopheses by "Click" Reactions: Synthesis and Analysis via LC-ESI-TOF MS," 2010, Macromolecules, 43:8436-8446.
Fiandanese, V., et al., "A Straightforward Synthesis of Benzofuran- and Indole-Substituted 1,2,3-Triazoles via Click Chemistry," 2009, Synthesis, 22:3853-3859, 7 pages.
Flynn, B.L., et al., "Discovery of 7-Hydroxy-6-methoxy-2-methyl-3-(3,4,5-trimethoxybenzoyl)benzo[b]furan (BNC105), a Tubulin Polymerization Inhibitor with Potent Antiproliferative and Tumor Vascular Disrupting Properties," 2011, J Med Chem, 54:6014-6027.
Geerts, S., et al., "Anthelmintic Resistance in Human Helminths: Learning From the Problems with Worm Control in Livestock," 1997, Parasitology Today 13:149-151.
Güven, O.O., "Synthesis and Characterization of Some Novel 4-Furyl Substituted 3-Imidazoline 3-0xides," 2007, Arkivoc, (xv):142-147.
Hackney, R.W., et al., "Marigold, Castor Bean, and Chrysanthemum as Controls of *Meliodogyne incognita* and *Pratylenchus alleni*," 1975, J Nematol 7/1:84-90.
Hwang, E., et al., "Semiconducting polymer thin films by surface-confined stepwise click polymerization" 2011, Supporting Information, Electronic Supplementary Material (ESI) for Chem Comm, 15 pages.
Ito et al. A medium-term rat liver bioassay for rapid in vivo detection of carcinogenic potential of chemicals. Cancer Science, 2003, 94:3-8.
Ito, S., et al., "a Facile Synthesis of 2,5-Disubstituted Tetrazoles by the Reaction of Phenylsulfonylhydrazones with Arenediazonium Salts," 1976, Bull Chem Soc JP, 49/7:1920-1923.
Kang, S.Y., et al., "Tetrazole-Biarylpyrazole Derivatives as Cannabinoid CB1 receptor Antagonists," 2008, Bioorg & Medic Chem Ltrs, 18:2385-2389.
Kinzel, T., et al., "A New Palladium Precatalyst Allows for the Fast Suzuki-Miyaura Coupling Reactions of Unstable Polyfluorophenyl and 2-Heteroaryl Boronic Acids," 2010, JACS, 132:14073-14075, 3 pages.
Klyuchnikova, O.A., et al., "Some Reactions of Tetrazolylthiopheses," 2005, Izvestiya Vysshikh Uchebnykh Zavedenii, Khimiya i Khimicheskaya Tekhnologiya, 48/10:53-58 (English abstract only).
Kumar, D., et al., "An Efficient, One-Pot, Regioselective Synthesis of I,4-Diaryl-1H-1,2,3-triazoles Using Click Chemistry," 2010, Synthesis, 10:1687-1691, 5 pages.
Lack, N. A. et al., "Correction to Targeting the Binding Function 3 (BF3) Site of the Human Androgen Receptor through Virtual Screening", Journal of Medicinal Chemistry, Dec. 28, 2001, 55/1:565-565, XP055265829.
Caplus printout of Latif et al. Carbonyl and thiocarbonyl compounds. Part XVII. Newer polyhalo-1,3-benzodioxoles and carbamates incorporating methylenedioxyphenyl structure. Indian Journal of Chemistry, Section B: Organic Chemistry Including Medicinal Chemistry. 1980, 19B:975-979.
Lörincz et al., "The Sequential Sonogashira-Click Reaction: A Versatile 4-Aryl-1,2,3-triazoles," 2009, Synthesis, 20:3527-3532.
Machida et al., "Photochemistry of the nitrogen-thiocarbonyl systems. Part 1. Photo induced reactions. Part 68. Photocycloaddition of arylcarbothioamides with unsaturated systems. Synthesis of 3,5-diaryl-1,2,4-thiadiazoles and 3-aryl-4,4,5,5-tramethylisothiazolines via photogenerated nitrile sulfides," 1984, Tetrahedron Ltrs, 25/4:409-10, Caplus, Document No. 100:174747, 2 pages.
Mishra et al. Basics and Potential Applications of Surfactants—A review. International Journal of PharmTech Research, 2009,1:1354-1365.
Nelson, D.W., et al., "Structure-Activity Relationship Studies on a Series of Novel, Substituted 1-Benzyl-5-Phenyltetrazole P2X67 Antagonists," 2006, J Med Chem, 49:3659-3666.
Nia, Al.S., et al., "Hydrogen-bonded perylene/terthiophene-materials: synthesis and spectroscopic properties," 2012, Tetrahedron, 68:722-729.

(56) References Cited

OTHER PUBLICATIONS

Obukhov, A.E., "Localization of the pump-induced electron interaction and of spin-orbital coupling or the near-lying singlet and triplet excited states in the impurity generation of light in the series multiatomic molecules," 2004, Proceedings of SPIE—The International Society for Optical Engineering, 5402:400-411.

Pan, S., et al., "Iron-Catalyzed N-Alkylation of Azoles via Oxidation of C-H Bond Adjacent to an Oxygen Atom", Organic Letters, May 7, 2010, 12/9:1932-1935, 4 pages.

CAPLUS 2011:1692287, Passarotti, C.M. et al., "Antiinflammatory activity of some 4-substituted-5-aminopyrazole derivatives", Currents in Toxicology and Therapy, 1(2), 89-93, CODEN: CTOTEG ISSN: 1122-3804, 1993, 23 pages.

Patsenker et al., "Acylation of 5-phenyl-2-(fur-2-yl)oxazole," 1997, Chem Hetero Compounds, 33/11:1277-1271, XP055136874.

Potratz, S., et al., "Thiophese-based Donor-Acceptor Co-Oligomers by Copper-Catalyzed 1,3-Dipolar Cycloaddition," 2012, Beilstein J Org Chem, 8:683-692.

Prichard, R., "Anthelmintic Resistance," 1994, Veterinary Parasitology, 54:259-268.

Pulici et al., "Trifluoroacetic Anhydride-Mediated Soled-Phase Version of the Robinson-Gabriel Synthesis of Oxazoles," 2005, J Combinatorial Chem, 7/3:463-473, XP055136879.

Sangster, N.C., et al., "Pharmacology of Anthelmintic Resistance," 1999, Parasitology Today 15/4:141-146.

Schillinger, E-K., et al., "Oligothiophene Versus β-Sheet Peptide: Synthesis and Self-Assembly of an Organic Semiconductor-Peptide Hybrid," 2009, Advanced Materials, 21:1562-1567.

Shang, Z., "Oxidative c-Cyclization of Aromatic Aldehyde N-acylhdrazones by bis(trifluoroacertoxy)iodobenzene," 2006, Synthetic Communications, 36/20:2927-2937.

Shaytan, A.K., et al., "Self-Assembling Nanofibers from Thiophene-Peptide Diblock Oligomers: A Combined Experimental and Computer Simulations Study," 2011, ACS Nano, 5/9:6894-6909, 16 pages.

Shawali, A.S., et al., "Azo Coupling of Benzenesulfonylhydrazones of Heterocyclic Aldehydes," 1979, J Heterocyclic Chem, 16/1:123-128, Wiley-Blackwell Publishing, Inc., XP002623113.

Shkumat, A.P., et al, "2-(2-furyl)- and 2-(2-thienyl)-5aryloxazoles," 1987, Ukrainskii Khimicheskii Zhurnal, 53/5:529-533, XP-002728980, Caplus Record 1988:75262, 1 page.

Smith, N.D., et al., "Discovery of Highly Potent, Selective, Orally Bioavailable, Metabotropic Glutamate Subtype 5 (mGlu5) Receptor Antagonists Devoid of Cytochrome P450 1A2 Inhibitory Activity," 2004, Biorganic & Medicinal Chemistry Letters, 14/22:5481-5484, Pergamon, Elsevier Science, GB, XP004598578.

Sung, H-H., et al., "Novel Alternating Fluorene-based Conjugated Polymers Containing Oxadiazole Pendants with Various Terminal Groups," 2004, Macromolecules, 37/21:7945-7954.

Yan et al., "Organic reactions in ionic liquids. Oxidative dimerisation of thioamides with phenyliodine(III) diacetate," 2003, J Chem Res, 10:618-619, Caplus, Doc No. 1400.357270.

Wagner, G., et al., "Hit-to-Lead Optimization of Disubstituted Oxadiazoles and Tetrazoles as mGluR5 NAMS," 2010, Bioorg & Medic Chem Ltrs, 20:3737-3741.

Weaver, G.W., "Product Class 8: 1,3,4-Oxadiazoles," 2004, Science of Synthesis, 13:219-251, 35 pages.

Zhang, Z., et al., "Studies on the synthesis and biological activity of 2-aryl-5-(5-methylisoxazole-3-yl)-1, 3, 4-oxadiazole derivatives and related property", 1992, Lanzhou Daxue Xuebao, ZiranKexueban, 28/2:103-111 (English Abstract only).

\* cited by examiner

N-,C-DISUBSTITUTED AZOLES AND COMPOSITIONS AND METHODS FOR CONTROLLING NEMATODE PESTS

REFERENCE TO RELATED APPLICATIONS

This application is a continuation of U.S. patent application Ser. No. 15/195,331, filed Jun. 28, 2016; which is a divisional of U.S. patent application Ser. No. 14/865,000, filed Sep. 25, 2015, now U.S. Pat. No. 9,402,397, issued Aug. 2, 2016; which is a divisional of U.S. patent application Ser. No. 14/210,917, filed Mar. 14, 2014, now U.S. Pat. No. 9,173,401, issued Nov. 3, 2015; and claims the benefit of U.S. Provisional Application Ser. No. 61/787,971, filed Mar. 15, 2013, the entire contents of which are incorporated herein by reference.

FIELD

Provided herein are new N-,C-disubstituted azoles and derivatives thereof that exhibit nematicidal activity and are useful, for example, in methods for the control of unwanted nematodes.

BACKGROUND

Nematodes are active, flexible, elongate organisms that live on moist surfaces or in liquid environments, including films of water within soil and moist tissues within other organisms. Many species of nematodes have evolved to be very successful parasites of plants and animals and, as a result, are responsible for significant economic losses in agriculture and livestock.

Plant parasitic nematodes can infest all parts of the plant, including the roots, developing flower buds, leaves, and stems. Plant parasites can be classified on the basis of their feeding habits into a few broad categories: migratory ectoparasites, migratory endoparasites, and sedentary endoparasites. Sedentary endoparasites, which include root knot nematodes (*Meloidogyne*) and cyst nematodes (*Globodera* and *Heterodera*), can establish long-term infections within roots that may be very damaging to crops.

There is an urgent need in the industry for effective, economical, and environmentally safe methods of controlling nematodes.

SUMMARY

There is now provided a N-,C-disubstituted azole of Formula I or a salt thereof,

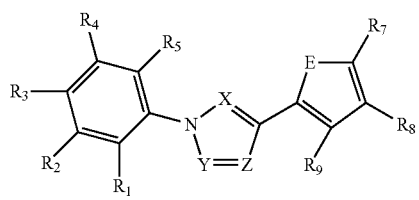

Formula I wherein $R_1$ and $R_5$ are independently selected from the group consisting of hydrogen, halogen, $CH_3$, $CF_3$, and $OCF_3$; $R_2$ and $R_4$ are independently selected from the group consisting of hydrogen, halogen, and $CF_3$; $R_3$ is selected from the group consisting of hydrogen, halogen, $CH_3$, $CF_3$, $OCF_3$, $OCH_3$, CN, and C(H)O; $R_7$, $R_8$ and $R_9$ are independently selected from the group consisting of hydrogen, halogen, $CH_3$, and $OCF_3$; X is N or C; Y is N or C; and Z is N or C, with the proviso that at least one of X, Y, and Z is C; and E is selected from the group consisting of O, S, and N—$R_{10}$, wherein $R_{10}$ is alkyl.

There is also provided a N-,C-disubstituted azole of Formula II or a salt thereof,

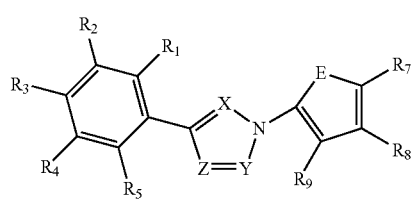

Formula II wherein $R_1$ and $R_5$ are independently selected from the group consisting of hydrogen, halogen, $CH_3$, $CF_3$, and $OCF_3$; $R_2$ and $R_4$ are independently selected from the group consisting of hydrogen, halogen, and $CF_3$; $R_3$ is selected from the group consisting of hydrogen, halogen, $CH_3$, $CF_3$, $OCF_3$, $OCH_3$, CN, and C(H)O; $R_7$, $R_8$ and $R_9$ are independently selected from the group consisting of hydrogen, halogen, $CH_3$, and $OCF_3$; X is N or C; Y is N or C; and Z is N or C, with the proviso that at least one of X, Y, and Z is C; and E is selected from the group consisting of O, S, and N—$R_{10}$, wherein $R_{10}$ is alkyl.

There is still further provided a N-,C-disubstituted azole of Formula III or a salt thereof,

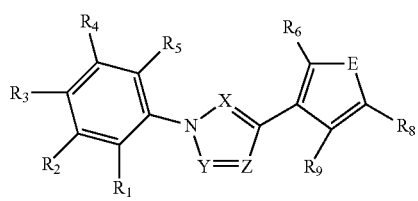

Formula III wherein $R_1$ and $R_5$ are independently selected from the group consisting of hydrogen, halogen, $CH_3$, $CF_3$, and $OCF_3$; $R_2$ and $R_4$ are independently selected from the group consisting of hydrogen, halogen, and $CF_3$; $R_3$ is selected from the group consisting of hydrogen, halogen, $CH_3$, $CF_3$, $OCF_3$, $OCH_3$, CN, and C(H)O; $R_6$, $R_8$ and $R_9$ are independently selected from the group consisting of hydrogen, halogen, $CH_3$, and $OCF_3$; X is N or C; Y is N or C; and Z is N or C, with the proviso that at least one of X, Y, and Z is C; and E is selected from the group consisting of O, S, and N—$R_{10}$, wherein $R_{10}$ is alkyl.

There is still further provided a N-,C-disubstituted azole of Formula IV or a salt thereof,

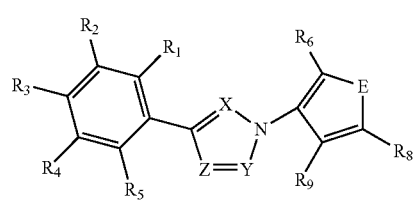

Formula IV wherein $R_1$ and $R_5$ are independently selected from the group consisting of hydrogen, halogen, $CH_3$, $CF_3$, and $OCF_3$; $R_2$ and $R_4$ are independently selected from the group consisting of hydrogen, halogen, and $CF_3$; $R_3$ is selected from the group consisting of hydrogen, halogen, $CH_3$, $CF_3$, $OCF_3$, $OCH_3$, CN, and C(H)O; $R_6$, $R_8$ and $R_9$ are independently selected from the group consisting of hydrogen, halogen, $CH_3$, and $OCF_3$; X is N or C; Y is N or C; and Z is N or C, with the proviso that at least one of X, Y, and Z is C; and E is selected from the group consisting of O, S, and N—$R_{10}$, wherein $R_{10}$ is alkyl.

There is still further provided a N-,C-disubstituted azole selected from the group consisting of: 4-(furan-2-yl)-1-phenyl-1H-1,2,3-triazole, or a salt thereof; 1-(2,4-difluorophenyl)-4-(thiophen-2-yl)-1H-1,2,3-triazole, or a salt thereof; 1-(4-chlorophenyl)-4-(furan-2-yl)-1H-1,2,3-triazole, or a salt thereof; 1-(4-fluorophenyl)-4-(furan-2-yl)-1H-1,2,3-triazole, or a salt thereof; 1-(2,4-difluorophenyl)-4-(furan-2-yl)-1H-1,2,3-triazole or a salt thereof 1-(4-chlorophenyl)-4-(thiophen-2-yl)-1H-1,2,3-triazole or a salt thereof; 1-phenyl-4-(thiophen-2-yl)-1H-pyrazole, or a salt thereof; 1-(4-chlorophenyl)-4-(thiophen-2-yl)-1H-pyrazole, or a salt thereof; 4-(furan-2-yl)-1-phenyl-1H-pyrazole, or a salt thereof; 1-(4-chlorophenyl)-4-(furan-2-yl)-1H-imidazole, or a salt thereof 1-(4-chlorophenyl)-4-(thiophen-2-yl)-1H-imidazole, or a salt thereof; 4-(furan-2-yl)-1-phenyl-1H-imidazole, or a salt thereof; 2-phenyl-4-(thiophen-2-yl)-2H-1,2,3-triazole, or a salt thereof; 4-(furan-2-yl)-2-phenyl-2H-1,2,3-triazole, or a salt thereof; 4-(2,4-difluorophenyl)-1-(thiophen-2-yl)-1H-1,2,3-triazole, or a salt thereof; 1-(furan-2-yl)-4-phenyl-1H-1,2,3-triazole, or a salt thereof 4-(4-fluorophenyl)-1-(thiophen-2-yl)-1H-1,2,3-triazole, or a salt thereof 4-(4-chlorophenyl)-1-(furan-2-yl)-1H-1,2,3-triazole, or a salt thereof, 4-phenyl-1-(thiophen-2-yl)-1H-pyrazole, or a salt thereof; 4-(4-chlorophenyl)-1-(thiophen-2-yl)-1H-pyrazole, or a salt thereof 1-(furan-2-yl)-4-phenyl-1H-pyrazole, or a salt thereof; 4-(4-chlorophenyl)-1-(thiophen-2-yl)-1H-imidazole, or a salt thereof; 1-(furan-2-yl)-4-phenyl-1H-imidazole, or a salt thereof; 4-phenyl-1-(thiophen-2-yl)-1H-imidazole, or a salt thereof 4-(4-chlorophenyl)-1-(furan-2-yl)-1H-imidazole, or a salt thereof; 4-phenyl-2-(thiophen-2-yl)-2H-1,2,3-triazole, or a salt thereof; 4-(furan-3-yl)-1-phenyl-1H-1,2,3-triazole, or a salt thereof; 1-phenyl-4-(thiophen-3-yl)-1H-pyrazole, or a salt thereof; 1-(4-chlorophenyl)-4-(thiophen-3-yl)-1H-pyrazole, or a salt thereof; 1-(4-chloro-2-methylphenyl)-4-(furan-3-yl)-1H-imidazole, or a salt thereof 2-phenyl-4-(thiophen-3-yl)-2H-1,2,3-triazole, or a salt thereof; 4-(furan-3-yl)-2-phenyl-2H-1,2,3-triazole, or a salt thereof 4-(2,4-difluorophenyl)-1-(thiophen-3-yl)-1H-1,2,3-triazole, or a salt thereof 1-(furan-3-yl)-4-phenyl-1H-1,2,3-triazole, or a salt thereof; 4-(4-chlorophenyl)-1-(thiophen-3-yl)-1H-pyrazole, or a salt thereof; 4-(4-chlorophenyl)-1-(thiophen-3-yl)-1H-imidazole, or a salt thereof; 1-(furan-3-yl)-4-phenyl-1H-imidazole, or a salt thereof 4-phenyl-1-(thiophen-3-yl)-1H-imidazole, or a salt thereof; and 4-(4-chlorophenyl)-2-(furan-3-yl)-2H-1,2,3-triazole, or a salt thereof.

There is also provided an aqueous nematicidal composition comprising an N-,C-disubstituted azole as described herein.

There is also provided a seed comprising a coating comprising an N-,C-disubstituted azole or nematicidal composition as described herein.

There is still further provided a method of controlling unwanted nematodes, the method comprising administering to mammals, birds, or their food, plants, seeds, or soil a composition comprising an effective amount of an N-,C-disubstituted azole as described herein.

Other objects and features will be in part apparent and in part pointed out hereinafter.

DETAILED DESCRIPTION

Described herein are new N-,C-disubstituted azoles and derivatives thereof that exhibit nematicidal activity. The compounds described herein may be used in the preparation of nematicidal compositions and in accordance with methods for control of unwanted nematodes, as set forth in detail below.

For example, in one embodiment, the compound is an N-,C-disubstituted azole of Formula I or a salt thereof,

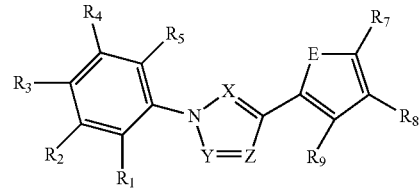

Formula I wherein $R_1$ and $R_5$ are independently selected from the group consisting of hydrogen, halogen, $CH_3$, $CF_3$, and $OCF_3$; $R_2$ and $R_4$ are independently selected from the group consisting of hydrogen, halogen, and $CF_3$; $R_3$ is selected from the group consisting of hydrogen, halogen, $CH_3$, $CF_3$, $OCF_3$, $OCH_3$, CN, and C(H)O; $R_7$, $R_8$ and $R_9$ are independently selected from the group consisting of hydrogen, halogen, $CH_3$, and $OCF_3$; X is N or C; Y is N or C; and Z is N or C, with the proviso that at least one of X, Y, and Z is C; and E is selected from the group consisting of O, S, and N—$R_{10}$, wherein $R_{10}$ is alkyl.

In one embodiment, the compound is an N-,C-disubstituted azole of Formula I or a salt thereof, with the proviso that when X is C, Y is N, Z is N, and E is S, at least one of $R_1$ through $R_5$ and $R_7$ through $R_9$ is other than hydrogen.

In another embodiment, the compound is a compound of Formula I or a salt thereof, with the proviso that when X is C, Y is N, Z is C, E is S, and $R_1$, $R_2$, $R_4$, $R_5$, and $R_7$ through $R_9$ are each hydrogen, $R_3$ is other than F.

In another embodiment, the compound is a compound of Formula I or a salt thereof, with the proviso that when X is N, Y is C, Z is C, and E is S, at least one of $R_1$ through $R_5$ and $R_7$ through $R_9$ is other than hydrogen.

For example, the compound of Formula I may be a 1,4-disubstituted-1H-1,2,3-triazole of Formula Ia or a salt thereof,

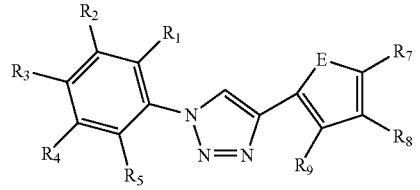

Formula Ia wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and CF$_3$; R$_3$ is selected from the group consisting of hydrogen, CH$_3$, CF$_3$, F, Cl, Br, OCF$_3$, OCH$_3$, CN, and C(H)O; R$_7$, R$_8$ and R$_9$ are independently selected from the group consisting of hydrogen, F, Cl, Br, CH$_3$, and OCF$_3$; and E is selected from the group consisting of O, S, and N—R$_{10}$, wherein R$_{10}$ is alkyl.

In one embodiment, the compound is a compound of Formula Ia or a salt thereof, with the proviso that when E is S, at least one of R$_1$ through R$_5$ and R$_7$ through R$_9$ is other than hydrogen.

Alternatively, the compound may be a 1,4-disubstituted-1H-pyrazole of Formula Ib or a salt thereof,

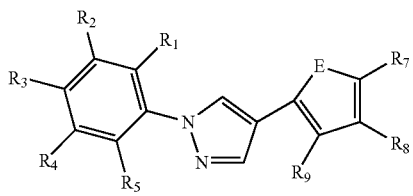

Formula Ib wherein R$_1$ and R$_5$ are independently selected from the group consisting of hydrogen, CH$_3$, F, Cl, Br, CF$_3$, and OCF$_3$; R$_2$ and R$_4$ are independently selected from the group consisting of hydrogen, F, Cl, Br, and CF$_3$; R$_3$ is selected from the group consisting of hydrogen, CH$_3$, CF$_3$, F, Cl, Br, OCF$_3$, OCH$_3$, CN, and C(H)O; R$_7$, R$_8$ and R$_9$ are independently selected from the group consisting of hydrogen, F, Cl, Br, CH$_3$, and OCF$_3$; and E is selected from the group consisting of O, S, and N—R$_{10}$, wherein R$_{10}$ is alkyl.

In one embodiment, the compound is a 1,4-disubstituted-1H-pyrazole of Formula Ib or a salt thereof, with the proviso that when E is S and R$_1$, R$_2$, R$_4$, R$_5$, and R$_7$ through R$_9$ are each hydrogen, R$_3$ is other than F.

Alternatively, the compound may be a 1,4-disubstituted-1H-imidazole of Formula Ic or a salt thereof,

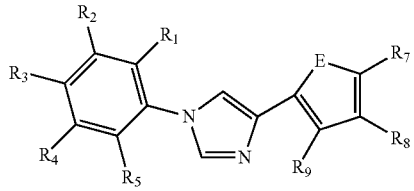

Formula Ic wherein R$_1$ and R$_5$ are independently selected from the group consisting of hydrogen, CH$_3$, F, Cl, Br, CF$_3$, and OCF$_3$; R$_2$ and R$_4$ are independently selected from the group consisting of hydrogen, F, Cl, Br, and CF$_3$; R$_3$ is selected from the group consisting of hydrogen, CH$_3$, CF$_3$, F, Cl, Br, OCF$_3$, OCH$_3$, CN, and C(H)O; R$_7$, R$_8$ and R$_9$ are independently selected from the group consisting of hydrogen, F, Cl, Br, CH$_3$, and OCF$_3$; and E is selected from the group consisting of O, S, and N—R$_{10}$, wherein R$_{10}$ is alkyl.

Alternatively, the compound may be a 2,4-disubstituted-2H-1,2,3-triazole of Formula Id or a salt thereof.

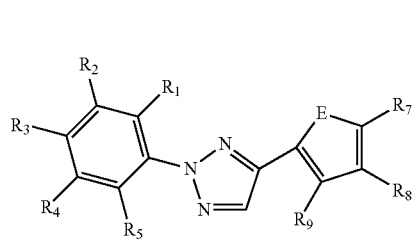

Formula Id wherein R$_1$ and R$_5$ are independently selected from the group consisting of hydrogen, CH$_3$, F, Cl, Br, CF$_3$, and OCF$_3$; R$_2$ and R$_4$ are independently selected from the group consisting of hydrogen, F, Cl, Br, and CF$_3$; R$_3$ is selected from the group consisting of hydrogen, CH$_3$, CF$_3$, F, Cl, Br, OCF$_3$, OCH$_3$, CN, and C(H)O; R$_7$, R$_8$ and R$_9$ are independently selected from the group consisting of hydrogen, F, Cl, Br, CH$_3$, and OCF$_3$; and E is selected from the group consisting of O, S, and N—R$_{10}$, wherein R$_{10}$ is alkyl.

In another embodiment, the compound is an N-,C-disubstituted azole of Formula II or a salt thereof,

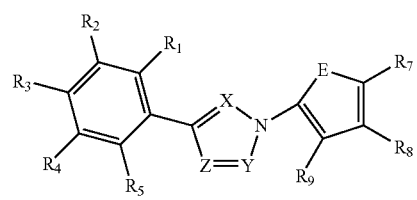

Formula II wherein R$_1$ and R$_5$ are independently selected from the group consisting of hydrogen, halogen, CH$_3$, CF$_3$, and OCF$_3$; R$_2$ and R$_4$ are independently selected from the group consisting of hydrogen, halogen, and CF$_3$; R$_3$ is selected from the group consisting of hydrogen, halogen, CH$_3$, CF$_3$, OCF$_3$, OCH$_3$, CN, and C(H)O; R$_7$, R$_8$ and R$_9$ are independently selected from the group consisting of hydrogen, halogen, CH$_3$, and OCF$_3$; X is N or C; Y is N or C; and Z is N or C, with the proviso that at least one of X, Y, and Z is C; and E is selected from the group consisting of O, S, and N—R$_{10}$, wherein R$_{10}$ is alkyl.

In one embodiment, the compound is an N-,C-disubstituted azole of Formula II or a salt thereof, with the proviso that when X is C, Y is N, Z is N, and E is S, at least one of R$_1$ to R$_5$ and R$_7$ to R$_9$ is other than hydrogen, and further provided that when X is C, Y is N, Z is N, E is S, and R$_1$, R$_2$, R$_4$, R$_5$, and R$_7$ through R$_9$ are each hydrogen, R$_3$ is other than CH$_3$.

For example, the compound of Formula II may be a 1,4-disubstituted-1H-1,2,3-triazole of Formula IIa or a salt thereof,

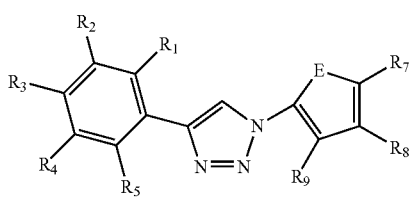

Formula IIa wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_7$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

In one embodiment, the compound is a 1,4-disubstituted-1H-1,2,3-triazole of Formula IIa or a salt thereof, with the proviso that when E is S, at least one of $R_1$ to $R_5$ or $R_7$ to $R_9$ is other than hydrogen, and further provided that when E is S and $R_1$, $R_2$, $R_4$, $R_5$, and $R_7$ through $R_9$ are each hydrogen, $R_3$ is other than $CH_3$.

Alternatively, the compound may be a 1,4-disubstituted-1H-pyrazole of Formula IIb or a salt thereof,

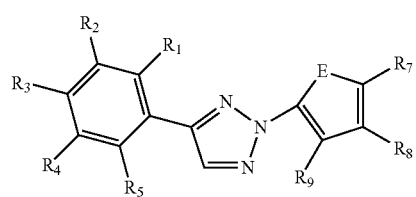

Formula IIb wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_7$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

Alternatively, the compound is a 1,4-disubstituted-1H-imidazole of Formula IIc or a salt thereof,

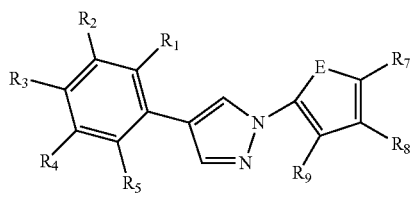

Formula IIc wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_7$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

Alternatively, the compound is a 2,4-disubstituted-1H-1,2,3-triazole of Formula IId or a salt thereof,

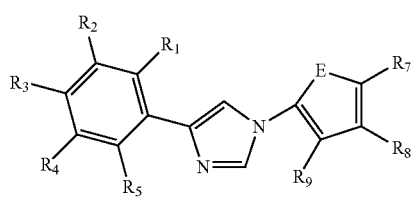

Formula IId wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_7$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

In another embodiment, the compound is an N-,C-disubstituted azole of Formula III or a salt thereof,

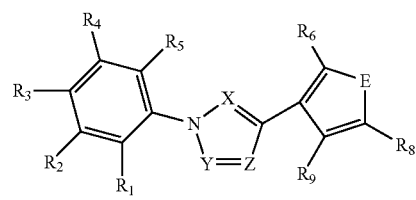

Formula III wherein $R_1$ and $R_5$ are independently selected from the group consisting of hydrogen, halogen, $CH_3$, $CF_3$, and $OCF_3$; $R_2$ and $R_4$ are independently selected from the group consisting of hydrogen, halogen, and $CF_3$; $R_3$ is selected from the group consisting of hydrogen, halogen, $CH_3$, $CF_3$, $OCF_3$, $OCH_3$, CN, and C(H)O; $R_6$, $R_8$ and $R_9$ are independently selected from the group consisting of hydrogen, halogen, $CH_3$, and $OCF_3$; X is N or C; Y is N or C; and Z is N or C, with the proviso that at least one of X, Y, and Z is C; and E is selected from the group consisting of O, S, and N—$R_{10}$, wherein $R_{10}$ is alkyl.

In one embodiment, the compound is an N-,C-disubstituted azole of Formula III or a salt thereof, with the proviso that when X is C, Y is N, Z is N, and E is S, at least one of $R_1$ through $R_6$, $R_8$, and $R_9$ is other than hydrogen.

In another embodiment, the compound is a compound of Formula III or a salt thereof, with the proviso that when X is C, Y is N, Z is C, E is S, and $R_1$, $R_2$, $R_4$, $R_5$, $R_6$, $R_8$, and $R_9$ are each hydrogen, $R_3$ is other than F.

In another embodiment, the compound is a compound of Formula III or a salt thereof, with the proviso that when X is N, Y is C, Z is C, and E is S, at least one of $R_1$ through $R_6$, $R_8$, and $R_9$ is other than hydrogen.

For example, the compound may be a 1,4-disubstituted-1H-1,2,3-triazole of Formula IIIa or a salt thereof,

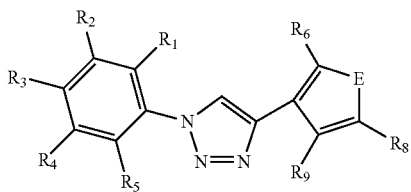

Formula IIIa wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

In one embodiment, the compound is a compound of Formula IIIa or a salt thereof, with the proviso that when E is S, at least one of $R_1$ through $R_6$, $R_8$, and $R_9$ is other than hydrogen.

Alternatively, the compound may be a 1,4-disubstituted-1H-pyrazole of Formula IIIb or a salt thereof,

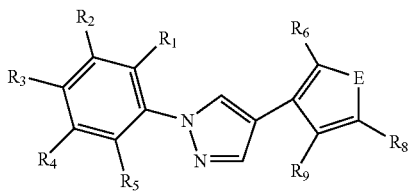

Formula IIIb wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

In one embodiment, the compound is a 1,4-disubstituted-1H-pyrazole of Formula IIIb or a salt thereof, with the proviso that when E is S and $R_1$, $R_2$, $R_4$, $R_5$, $R_6$, $R_8$, and $R_9$ are each hydrogen, $R_3$ is other than F.

Alternatively, the compound may be a 1,4-disubstituted-1H-imidazole of Formula IIIc or a salt thereof,

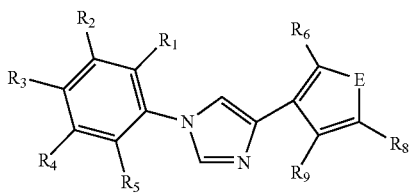

Formula IIIc wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

Alternatively, the compound may be a 2,4-disubstituted-2H-1,2,3-triazole of Formula IIId or a salt thereof,

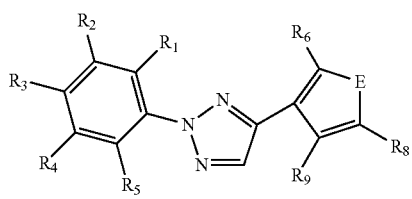

Formula IIId wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

In another embodiment, the compound is an N-,C-disubstituted azole of Formula IV or a salt thereof,

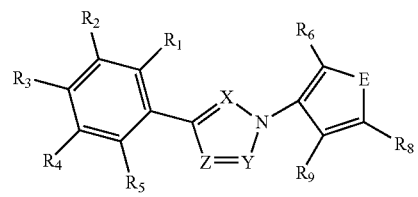

Formula IV wherein $R_1$ and $R_5$ are independently selected from the group consisting of hydrogen, halogen, $CH_3$, $CF_3$, and $OCF_3$; $R_2$ and $R_4$ are independently selected from the group consisting of hydrogen, halogen, and $CF_3$; $R_3$ is selected from the group consisting of hydrogen, halogen, $CH_3$, $CF_3$, $OCF_3$, $OCH_3$, CN, and C(H)O; $R_6$, $R_8$ and $R_9$ are independently selected from the group consisting of hydrogen, halogen, $CH_3$, and $OCF_3$; X is N or C; Y is N or C; and Z is N or C, with the proviso that at least one of X, Y, and Z is C; and E is selected from the group consisting of O, S, and N—$R_{10}$, wherein $R_{10}$ is alkyl.

In another embodiment, the compound is an N-,C-disubstituted azole of Formula IV or a salt thereof, with the proviso that when X is C, Y is N, Z is N, and E is S, at least one of $R_1$ through $R_6$, $R_8$, and $R_9$ is other than hydrogen.

In some embodiments, the compound is an N-,C-disubstituted azole of Formula IV or a salt thereof, with the proviso that when X is C, Y is N, Z is N, E is S, and $R_1$, $R_2$, $R_4$, $R_5$, $R_6$, $R_8$, and $R_9$ are each hydrogen, $R_3$ is other than $CH_3$.

For example, the compound may be a 1,4-disubstituted-1H-1,2,3-triazole of Formula IVa or a salt thereof,

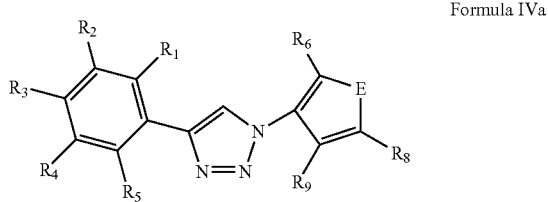

Formula IVa wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

In one embodiment, the compound is a 1,4-disubstituted-1H-1,2,3-triazole of Formula IVa or a salt thereof, with the proviso that when E is S, at least one of $R_1$ through $R_6$, $R_8$, and $R_9$ is other than hydrogen.

In some embodiments, the compound is a 1,4-disubstituted-1H-1,2,3-triazole of Formula IVa or a salt thereof, with the proviso that when E is S and $R_1$, $R_2$, $R_4$, $R_5$, $R_6$, $R_8$, and $R_9$ are each hydrogen, $R_3$ is other than $CH_3$.

Alternatively, the compound may be a 1,4-disubstituted-1H-pyrazole of Formula IVb or a salt thereof,

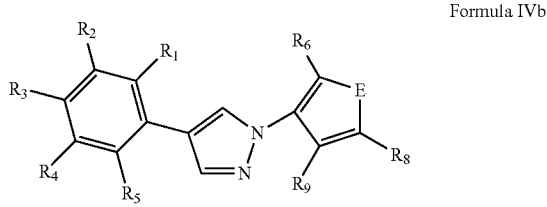

Formula IVb wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

Alternatively, the compound is a 1,4-disubstituted-1H-imidazole of Formula IVc or a salt thereof,

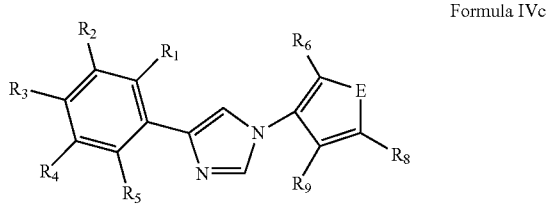

Formula IVc wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

Alternatively, the compound is a 2,4-disubstituted-2H-1,2,3-triazole of Formula IVd or a salt thereof,

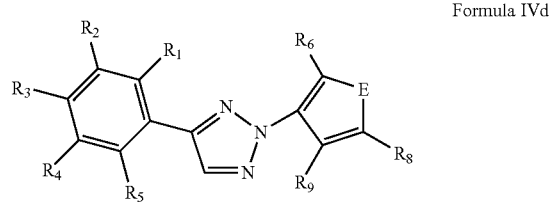

Formula IVd wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

In one embodiment, the compound is a compound of one of Formulas I through IId wherein each of $R_7$, $R_8$ and $R_9$ is hydrogen, or a compound of one of Formulas III through IVd wherein each of $R_6$, $R_8$ and $R_9$ is hydrogen. In some embodiments, each of $R_1$, $R_2$, $R_3$, $R_4$, and $R_5$ is also hydrogen. In other embodiments, at least one of $R_1$, $R_2$, $R_3$, $R_4$, and $R_5$ is other than hydrogen. For example, in some embodiments, at least one of $R_1$, $R_2$, $R_3$, $R_4$, and $R_5$ is halogen.

In some embodiments, the compound is a compound of one of Formulas I through IId wherein E is O or S. For example, in some embodiments, E is O. In other embodiments, E is S.

As used herein, the term "halo" or "halogen" refers to any radical of fluorine, chlorine, bromine or iodine.

The term "alkyl" as employed herein, by itself or as part of another group, refers to both straight and branched chain radicals of up to ten carbons, which may be optionally independently substituted. Non-limiting examples of $C_1$-$C_{10}$ alkyl groups include methyl, ethyl, propyl, isopropyl, butyl, sec-butyl, tert-butyl, 3-pentyl, hexyl and octyl groups, each of which may be optionally independently substituted.

As used herein, the term "N-,C-disubstituted azole" encompasses the substituted pyrrole, pyrazole, imidazole, and/or triazole compounds described herein. For example, the term "N-,C-disubstituted azole," or equivalently, "N-,C-disubstituted azole derivative" or "N-,C-disubstituted azole analog," encompasses the compounds of Formulas I, Ia, Ib, Ic, Id, II, IIa, IIb IIc, IId, III, IIIa, IIIb, IIIc, IIId, IV, IVa, IVb, IVc, and IVd as defined above.

Non-limiting examples of species include 4-(furan-2-yl)-1-phenyl-1H-1,2,3-triazole of Formula Ia-i, or a salt thereof,

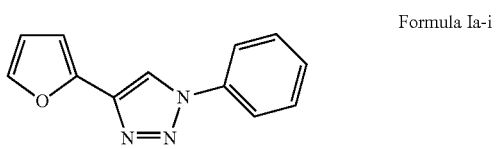 [SMILES: c1ccc(-n2cc(-c3cccs3)cn2)cc1]

Formula Ia-i 1-(2,4-difluorophenyl)-4-(thiophen-2-yl)-1H-1,2,3-triazole of Formula Ia-ii, or a salt thereof,

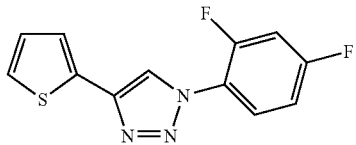
Formula Ia-ii 1-(4-chlorophenyl)-4-(furan-2-yl)-1H-1,2,3-triazole of Formula Ia-iii, or a salt thereof,

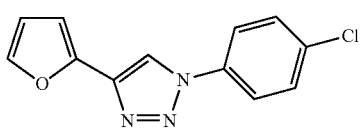
Formula Ia-iii 1-(4-fluorophenyl)-4-(furan-2-yl)-1H-1,2,3-triazole of Formula Ia-iv, or a salt thereof,

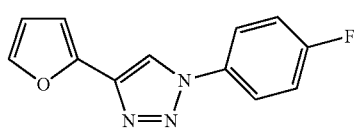
Formula Ia-iv 1-(2,4-difluorophenyl)-4-(furan-2-yl)-1H-1,2,3-triazole of Formula Ia-v, or a salt thereof,

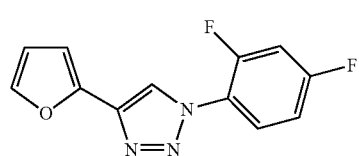
Formula Ia-v 1-phenyl-4-(thiophen-2-yl)-1H-1,2,3-triazole of Formula Ia-vi, or a salt thereof,

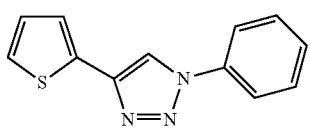
Formula Ia-vi 1-(4-chlorophenyl)-4-(thiophen-2-yl)-1H-1,2,3-triazole of Formula Ia-vii, or a salt thereof,

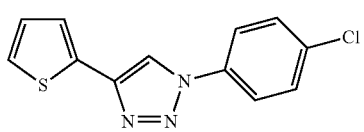
Formula Ia-vii 1-phenyl-4-(thiophen-2-yl)-1H-pyrazole of Formula Ib-i, or a salt thereof,

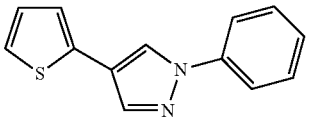
Formula Ib-i 1-(4-chlorophenyl)-4-(thiophen-2-yl)-1H-pyrazole of Formula Ib-ii, or a salt thereof,

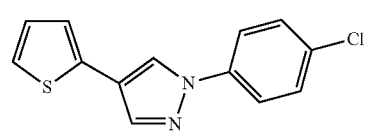
Formula Ib-ii 4-(furan-2-yl)-1-phenyl-1H-pyrazole of Formula Ib-iii, or a salt thereof,

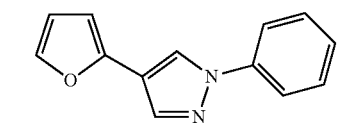
Formula Ib-iii 1-(4-chlorophenyl)-4-(furan-2-yl)-1H-imidazole of Formula Ic-i, or a salt thereof,

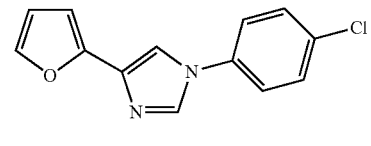
Formula Ic-i 1-(4-chlorophenyl)-4-(thiophen-2-yl)-1H-imidazole of Formula Ic-ii, or a salt thereof,

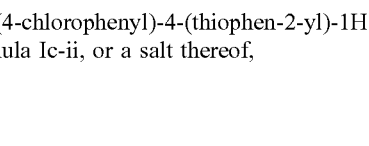
Formula Ic-ii 4-(furan-2-yl)-1-phenyl-1H-imidazole of Formula Ic-iii, or a salt thereof,

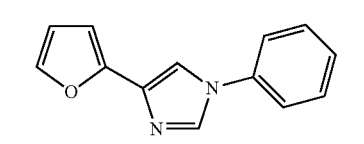
Formula Ic-iii 2-phenyl-4-(thiophen-2-yl)-2H-1,2,3-triazole of Formula Id-i, or a salt thereof,

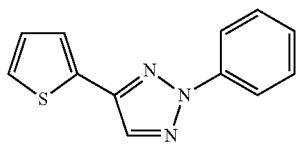

4-(furan-2-yl)-2-phenyl-2H-1,2,3-triazole of Formula Id-ii, or a salt thereof,

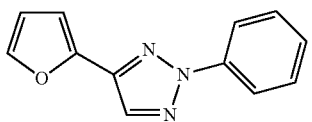

4-(2,4-difluorophenyl)-1-(thiophen-2-yl)-1H-1,2,3-triazole of Formula IIa-i, or a salt thereof,

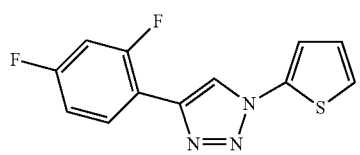

4-phenyl-1-(thiophen-2-yl)-1H-1,2,3-triazole of Formula IIa-ii, or a salt thereof,

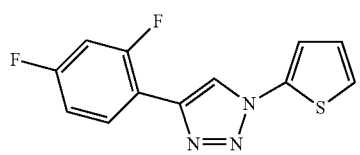

1-(furan-2-yl)-4-phenyl-1H-1,2,3-triazole of Formula IIa-iii, or a salt thereof,

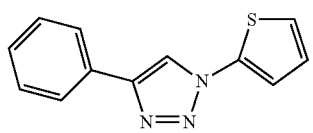

4-(4-fluorophenyl)-1-(thiophen-2-yl)-1H-1,2,3-triazole of Formula IIa-iv, or a salt thereof,

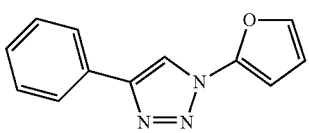

4-(4-chlorophenyl)-1-(furan-2-yl)-1H-1,2,3-triazole of Formula IIa-v, or a salt thereof,

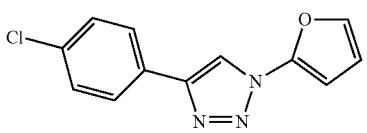

4-phenyl-1-(thiophen-2-yl)-1H-pyrazole of Formula Ib-i, or a salt thereof,

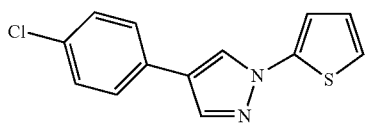

4-(4-chlorophenyl)-1-(thiophen-2-yl)-1H-pyrazole of Formula IIb-ii, or a salt thereof,

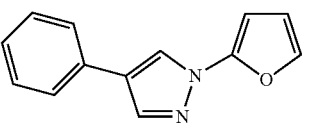

1-(furan-2-yl)-4-phenyl-1H-pyrazole of Formula IIb-iii, or a salt thereof,

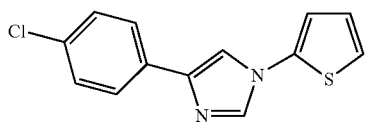

4-(4-chlorophenyl)-1-(thiophen-2-yl)-1H-imidazole of Formula IIc-i, or a salt thereof,

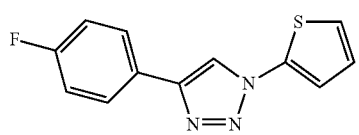

1-(furan-2-yl)-4-phenyl-1H-imidazole of Formula IIc-ii, or a salt thereof,

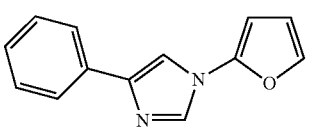

4-phenyl-1-(thiophen-2-yl)-1H-imidazole of Formula IIc-iii, or a salt thereof,

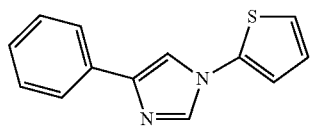

4-(4-chlorophenyl)-1-(furan-2-yl)-1H-imidazole of Formula IIc-iv, or a salt thereof,

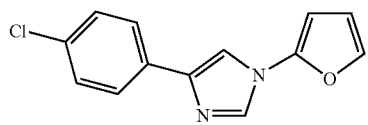

4-phenyl-2-(thiophen-2-yl)-2H-1,2,3-triazole of Formula IId-i, or a salt thereof,

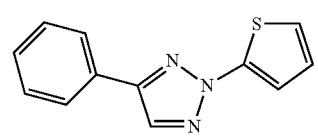

1-phenyl-4-(thiophen-3-yl)-1H-pyrazole of Formula IIIb-i, or a salt thereof,

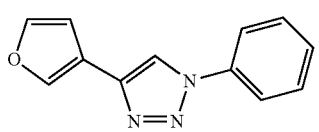

1-(4-chloro-2-methylphenyl)-4-(furan-3-yl)-1H-imidazole of Formula IIIc-i, or a salt thereof,

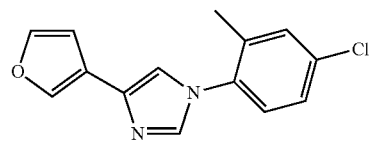

2-phenyl-4-(thiophen-3-yl)-2H-1,2,3-triazole of Formula IIId-i, or a salt thereof,

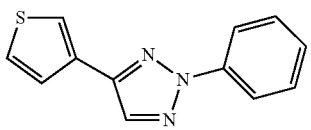

4-(furan-3-yl)-2-phenyl-2H-1,2,3-triazole of Formula IIId-ii, or a salt thereof,

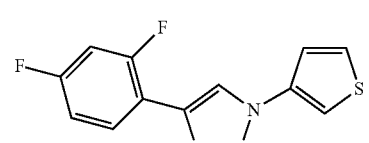

4-(2,4-difluorophenyl)-1-(thiophen-3-yl)-1H-1,2,3-triazole of Formula IVa-i, or a salt thereof,

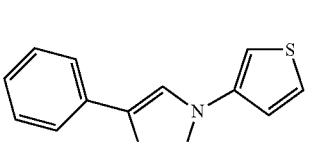

4-phenyl-1-(thiophen-3-yl)-1H-1,2,3-triazole of Formula IVa-ii, or a salt thereof,

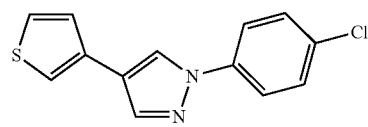

1-(furan-3-yl)-4-phenyl-1H-1,2,3-triazole of Formula IVa-iii, or a salt thereof,

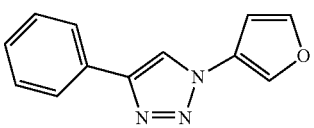

4-(4-chlorophenyl)-1-(thiophen-3-yl)-1H-pyrazole of Formula IVb-i, or a salt thereof,

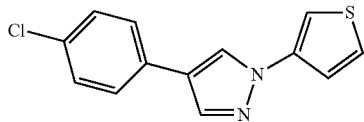

4-(4-chlorophenyl)-1-(thiophen-3-yl)-1H-imidazole of Formula IVc-i, or a salt thereof,

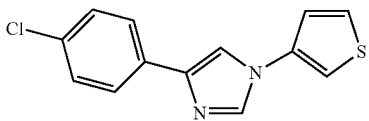

1-(furan-3-yl)-4-phenyl-1H-imidazole of Formula IVc-ii, or a salt thereof,

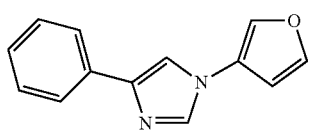

4-phenyl-1-(thiophen-3-yl)-1H-imidazole of Formula IVc-iii, or a salt thereof; and

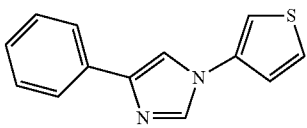

4-(4-chlorophenyl)-2-(furan-3-yl)-2H-1,2,3-triazole of Formula IVd-i, or a salt thereof.

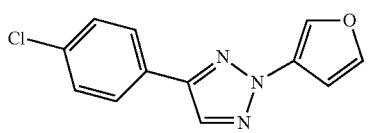

Methods of Use

Generally, the compounds described herein can be applied to seeds, plants, or the environment of plants needing nematode control, or to animals or the food of animals needing nematode parasite control.

For example, in one embodiment, the disclosure is generally related to a method for control of unwanted nematodes, the method comprising administering to mammals, birds, or their food, a plant, a seed or soil a composition comprising an effective amount of an N-,C-disubstituted azole as described herein.

In another embodiment, the method comprises administering to a plant, a seed or soil a composition comprising an effective amount of an N-,C-disubstituted azole as described herein.

Application to Seeds

One embodiment of the disclosure is generally related to a method of protecting a seed, and/or the roots of a plant or plant parts grown from the seed, against damage by a nematode. In one embodiment, the method comprises treating a seed with a seed treatment composition comprising a nematicidal compound as described herein.

The seed treatment methods described herein can be used in connection with any species of plant and/or the seeds thereof. In one embodiment, the methods are used in connection with seeds of plant species that are agronomically important. For example, the seeds can be of corn, peanut, canola/rapeseed, soybean, cucurbits, crucifers, cotton, beets, rice, sorghum, sugar beet, wheat, barley, rye, sunflower, tomato, sugarcane, tobacco, oats, as well as other vegetable and leaf crops. In some embodiments, the seed is corn, soybean, or cotton seed. The seed may be a transgenic seed from which a transgenic plant can grow and incorporates a transgenic event that confers, for example, tolerance to a particular herbicide or combination of herbicides, increased disease resistance, enhanced tolerance to stress and/or enhanced yield. Transgenic seeds include, but are not limited to, seeds of corn, soybean and cotton. The seed may comprise a breeding trait, including for example, a nematode breeding trait.

The seed treatment method may comprise applying the seed treatment composition to the seed prior to sowing the seed, so that the sowing operation is simplified. In this manner, seeds can be treated, for example, at a central location and then distributed for planting. This may permit a person who plants the seeds to avoid the complexity and effort associated with handling and applying the seed treatment compositions, and to merely plant the treated seeds in a manner that is conventional for regular untreated seeds.

The seed treatment composition can be applied to seeds by any standard seed treatment methodology, including but not limited to mixing in a container (e.g., a bottle or bag), mechanical application, tumbling, spraying, immersion, and solid matrix priming. Seed coating methods and apparatus for their application are disclosed in, for example, U.S. Pat. Nos. 5,918,413, 5,891,246, 5,554,445, 5,389,399, 5,107,787, 5,080,925, 4,759,945 and 4,465,017, among others. Any conventional active or inert material can be used for contacting seeds with the seed treatment composition, such as conventional film-coating materials including but not limited to water-based film coating materials.

For example, in one embodiment, a seed treatment composition can be introduced onto or into a seed by use of solid matrix priming. For example, a quantity of the seed treatment composition can be mixed with a solid matrix material and then the seed can be placed into contact with the solid matrix material for a period to allow the seed treatment composition to be introduced to the seed. The seed can then optionally be separated from the solid matrix material and stored or used, or the mixture of solid matrix material plus seed can be stored or planted directly. Non-limiting examples of solid matrix materials which are useful include polyacrylamide, starch, clay, silica, alumina, soil, sand, polyurea, polyacrylate, or any other material capable of absorbing or adsorbing the seed treatment composition for a time and releasing the nematicide of the seed treatment composition into or onto the seed. It is useful to make sure that the nematicide and the solid matrix material are compatible with each other. For example, the solid matrix material should be chosen so that it can release the nematicide at a reasonable rate, for example over a period of minutes, hours, days, or weeks.

Imbibition is another method of treating seed with the seed treatment composition. For example, a plant seed can be directly immersed for a period of time in the seed treatment composition. During the period that the seed is immersed, the seed takes up, or imbibes, a portion of the seed treatment composition. Optionally, the mixture of plant seed and the seed treatment composition can be agitated, for example by shaking, rolling, tumbling, or other means. After imbibition, the seed can be separated from the seed treatment composition and optionally dried, for example by patting or air drying.

The seed treatment composition may be applied to the seeds using conventional coating techniques and machines, such as fluidized bed techniques, the roller mill method, rotostatic seed treaters, and drum coaters. Other methods, such as spouted beds may also be useful. The seeds may be pre-sized before coating. After coating, the seeds are typically dried and then transferred to a sizing machine for sizing. Such procedures are generally known in the art.

If the seed treatment composition is applied to the seed in the form of a coating, the seeds can be coated using a variety of methods known in the art. For example, the coating process can comprise spraying the seed treatment composition onto the seed while agitating the seed in an appropriate piece of equipment such as a tumbler or a pan granulator.

In one embodiment, when coating seed on a large scale (for example a commercial scale), the seed coating may be applied using a continuous process. For example, seed may be introduced into the treatment equipment (such as a tumbler, a mixer, or a pan granulator) either by weight or by flow rate. The amount of treatment composition that is introduced into the treatment equipment can vary depending on the seed weight to be coated, surface area of the seed, the concentration of the nematicide and/or other active ingredients in the treatment composition, the desired concentration on the finished seed, and the like. The treatment composition can be applied to the seed by a variety of means, for example by a spray nozzle or revolving disc. The amount of liquid may be determined by the assay of the formulation and the required rate of active ingredient necessary for efficacy. As the seed falls into the treatment equipment the seed can be treated (for example by misting or spraying with the seed treatment composition) and passed through the treater under continual movement/tumbling where it can be coated evenly and dried before storage or use.

In another embodiment, the seed coating may be applied using a batch process. For example, a known weight of seeds can be introduced into the treatment equipment (such as a tumbler, a mixer, or a pan granulator). A known volume of seed treatment composition can be introduced into the treatment equipment at a rate that allows the seed treatment composition to be applied evenly over the seeds. During the application, the seed can be mixed, for example by spinning or tumbling. The seed can optionally be dried or partially dried during the tumbling operation. After complete coating, the treated sample can be removed to an area for further drying or additional processing, use, or storage.

In an alternative embodiment, the seed coating may be applied using a semi-batch process that incorporates features from each of the batch process and continuous process embodiments set forth above.

In still another embodiment, seeds can be coated in laboratory size commercial treatment equipment such as a tumbler, a mixer, or a pan granulator by introducing a known weight of seeds in the treater, adding the desired amount of seed treatment composition, tumbling or spinning the seed and placing it on a tray to thoroughly dry.

In another embodiment, seeds can also be coated by placing the known amount of seed into a narrow neck bottle or receptacle with a lid. While tumbling, the desired amount of seed treatment composition can be added to the receptacle. The seed is tumbled until it is coated with the treatment composition. After coating, the seed can optionally be dried, for example on a tray.

In some embodiments, the treated seeds may also be enveloped with a film overcoating to protect the nematicidal coating. Such overcoatings are known in the art and may be applied using conventional fluidized bed and drum film coating techniques. The overcoatings may be applied to seeds that have been treated with any of the seed treatment techniques described above, including but not limited to solid matrix priming, imbibition, coating, and spraying, or by any other seed treatment technique known in the art.

Application to Plants and/or Soil

In other various embodiments, the disclosure is generally related to protecting a plant against damage by a nematode. For example, in one embodiment, a treatment composition comprising a nematicidal compound (e.g., an N-,C-disubstituted azole or derivative thereof) as described herein may be supplied to a plant exogenously. The treatment composition may be applied to the plant and/or the surrounding soil through sprays, drips, and/or other forms of liquid application.

In another embodiment, a treatment composition comprising the compound is directly applied to the soil surrounding the root zone of a plant. Soil applications may require 0.5 to 2 kg per hectare on a broadcast basis (rate per treated area if broadcast or banded).

The application may be performed using any method or apparatus known in the art, including but not limited to hand sprayer, mechanical sprinkler, or irrigation, including drip irrigation.

For example, in one embodiment, the nematicidal treatment composition is applied to plants and/or soil using a drip irrigation technique. Preferably, the nematicidal treatment composition is applied directly to the base of the plants or the soil immediately adjacent to the plants. The composition may be applied through existing drip irrigation systems. This procedure is particularly preferred for use in connection with cotton, strawberries, tomatoes, potatoes, vegetables, and ornamental plants.

In another embodiment, the nematicidal treatment composition is applied to plants and/or soil using a drench application. Preferably, a sufficient quantity of the nematicidal treatment composition is applied such that it drains through the soil to the root area of the plants. The drench application technique is particularly preferred for use in connection with crop plants, turf grasses, and animals.

In some embodiments, the nematicidal composition is applied to soil after planting. In other embodiments, however, the nematicidal composition may be applied to soil during planting. In other embodiments, however, the nematicidal composition may be applied to soil before planting. When the nematicidal composition is applied directly to the soil, it may be applied using any method known in the art. For example, it may be tilled into the soil or applied in furrow.

Administration to Animals

In other various embodiments, the disclosure is generally related to a method of controlling unwanted nematodes, the method comprising administering to an animal a nematicidal treatment composition comprising a nematicidal compound (e.g., an N-,C-disubstituted azole or derivative thereof) as described herein. For example, in one embodiment, the nematicidal treatment composition may be administered to an animal orally to promote activity against internal parasitic nematodes. In another embodiment, the nematicidal treatment composition may be administered by injection of the host animal. In another embodiment, the nematicidal treatment composition may be administered to the host animal by topical application.

In some embodiments, the nematicidal composition is formulated for topical applications such as pour-ons, or for the use in tags or collars. In these embodiments, it is particularly preferred that the host animal is a non-human animal.

The nematicidal compositions described herein can be applied to any vertebrate animal (e.g., a bird or a mammal). The bird can be a domesticated fowl (e.g., a chicken, turkey, duck, or goose). The mammal can be a domesticated animal, e.g., a companion animal (e.g., a cat, dog, horse or rabbit) or livestock (e.g., a cow, sheep, pig, goat, alpaca or llama). Alternatively, the mammal can be a human.

In another embodiment the disclosure is generally related to a nematicidal feed for a non-human vertebrate, wherein the nematicidal feed comprises (a) a feed; and (b) a nematicidal composition comprising a compound (e.g., an N-,C-disubstituted azole or derivative thereof) as described herein. In some embodiments, the feed is selected from the group consisting of: soy, wheat, corn, sorghum, millet, alfalfa, clover, and rye. Another embodiment is directed to a method of supplementing an animal feed to include one or more of the nematicidal compounds described herein.

Treated Seeds

In one embodiment the disclosure is generally related to a seed that has been treated with a seed treatment composition comprising a compound (e.g., an N-,C-disubstituted azole or derivative thereof) as described herein. Typically, the seed has been treated with the seed treatment composition using one of the seed treatment methods set forth above, including but not limited to solid matrix priming, imbibition, coating, and spraying. The seed may be of any plant species, as described above.

The treated seeds may comprise the compound in an amount of at least about 0.1 mg/seed, from about 0.1 to about 1 mg/seed, or from about 0.1 to about 0.5 mg/seed.

Nematicidal Compositions

In another embodiment the disclosure is generally related to a nematicidal composition comprising an effective amount of an N-,C-disubstituted azole or derivative thereof as described herein. In some embodiments, the nematicidal composition may be an aqueous composition.

Generally, the nematicidal compositions described herein can comprise any adjuvants, excipients, or other desirable components known in the art. For example, in some embodiments, the nematicidal composition further comprises a surfactant.

Examples of anionic surfactants include alkyl sulfates, alcohol sulfates, alcohol ether sulfates, alpha olefin sulfonates, alkylaryl ether sulfates, arylsulfonates, alkylsulfonates, alkylaryl sulfonates, sulfosuccinates, mono- or diphosphate esters of polyalkoxylated alkyl alcohols or alkyl phenols, mono- or disulfosuccinate esters of alcohols or polyalkoxylated alkanols, alcohol ether carboxylates, phenol ether carboxylates. In one embodiment, the surfactant is an alkylaryl sulfonate.

Non-limiting examples of commercially available anionic surfactants include sodium dodecylsulfate (Na-DS, SDS), MORWET D-425 (a sodium salt of alkyl naphthalene sulfonate condensate, available from Akzo Nobel), MORWET D-500 (a sodium salt of alkyl naphthalene sulfonate condensate with a block copolymer, available from Akzo Nobel), sodium dodecylbenzene sulfonic acid (Na-DBSA) (available from Aldrich), diphenyloxide disulfonate, naphthalene formaldehyde condensate, DOWFAX (available from Dow), dihexylsulfosuccinate, and dioctylsulfosuccinate, alkyl naphthalene sulfonate condensates, and salts thereof.

Examples of non-ionic surfactants include sorbitan esters, ethoxylated sorbitan esters, alkoxylated alkylphenols, alkoxylated alcohols, block copolymer ethers, and lanolin derivatives. In accordance with one embodiment, the surfactant comprises an alkylether block copolymer.

Non-limiting examples of commercially available non-ionic surfactants include SPAN 20, SPAN 40, SPAN 80, SPAN 65, and SPAN 85 (available from Aldrich); TWEEN 20, TWEEN 40, TWEEN 60, TWEEN 80, and TWEEN 85 (available from Aldrich); IGEPAL CA-210, IGEPAL CA-520, IGEPAL CA-720, IGEPAL CO-210, IGEPAL CO-520, IGEPAL CO-630, IGEPAL CO-720, IGEPAL CO-890, and IGEPAL DM-970 (available from Aldrich); Triton X-100 (available from Aldrich); BRIJ S10, BRU S20, BRU 30, BRIJ 52, BRU 56, BRU 58, BRU 72, BRU 76, BRU 78, BRU 92V, BRIJ 97, and BRU 98 (available from Aldrich); PLURONIC L-31, PLURONIC L-35, PLURONIC L-61, PLURONIC L-81, PLURONIC L-64, PLURONIC L-121, PLURONIC 10R5, PLURONIC 17R4, and PLURONIC 31R1 (available from Aldrich); Atlas G-5000 and Atlas G-5002L (available from Croda); ATLOX 4912 and ATLOX 4912-SF (available from Croda); and SOLUPLUS (available from BASF), LANEXOL AWS (available from Croda).

Non-limiting examples of cationic surfactants include mono alkyl quaternary amine, fatty acid amide surfactants, amidoamine, imidazoline, and polymeric cationic surfactants.

In some embodiments, the nematicidal composition comprises a co-solvent in addition to water. Non-limiting examples of co-solvents that can be used include, ethyl lactate, methyl soyate/ethyl lactate co-solvent blends (e.g., STEPOSOL, available from Stepan), isopropanol, acetone, 1,2-propanediol, n-alkylpyrrolidones (e.g., the AGSOLEX series, available from ISP), a petroleum based-oil (e.g., AROMATIC series and SOLVESSO series available from Exxon Mobil), isoparaffinic fluids (e.g., ISOPAR series, available from Exxon Mobil), cycloparaffinic fluids (e.g., NAPPAR 6, available from Exxon Mobil), mineral spirits (e.g., VARSOL series available from Exxon Mobil), and mineral oils (e.g., paraffin oil).

Examples of commercially available organic solvents include pentadecane, ISOPAR M, ISOPAR V, and ISOPAR L (available from Exxon Mobil).

In some embodiments, the nematicidal composition of N-,C-disubstituted azole may be formulated, mixed in a seed treater tank, combined on the seed by overcoating, or combined with one or more additional active ingredients. The additional active ingredients may comprise, for example, a pesticide or biopesticide. In some embodiments, the nematicidal composition comprises N-,C-disubstituted azole and another pesticide, for example a nematicide, insecticide, fungicide, herbicide, and/or other chemical.

In some embodiments, the nematicidal composition further comprises a second pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, chlorothalonil, propiconazole, tebuconazole and pyraclostrobin. The composition may also comprise herbicides (e.g., trifloxysulfuron, glyphosate, halosulfuron) and/or other chemicals useful for disease control (e.g., chitosan).

Non-limiting examples of insecticides and nematicides include carbamates, diamides, macrocyclic lactones, neonicotinoids, organophosphates, phenylpyrazoles, pyrethrins, spinosyns, synthetic pyrethroids, tetronic and tetramic acids. In another embodiment, insecticides and nematicides include abamectin, aldicarb, aldoxycarb, bifenthrin, carbofuran, chlorantraniliprole, clothianidin, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, 3-phenyl-5-(thiophen-2-yl)-1,2,4-oxadiazole, nitenpyram, oxamyl, permethrin, spinetoram, spinosad, spirodichlofen, spirotetramat, tefluthrin, thiacloprid, thiamethoxam, and thiodicarb.

Non-limiting examples of useful fungicides include aromatic hydrocarbons, benzimidazoles, benzothiadiazole, carboxamides, carboxylic acid amides, morpholines, phenylamides, phosphonates, quinone outside inhibitors (e.g. strobilurins), thiazolidines, thiophanates, thiophene carboxamides, and triazoles, Non-limiting examples of fungicides include acibenzolar-S-methyl, azoxystrobin, benalaxyl, bixafen, boscalid, carbendazim, cyproconazole, dimethomorph, epoxiconazole, fluopyram, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thifluzamide, thiophanate, tolclofos-methyl, trifloxystrobin, and triticonazole.

Non-limiting examples of herbicides include ACCase inhibitors, acetanilides, AHAS inhibitors, carotenoid biosynthesis inhibitors, EPSPS inhibitors, glutamine synthetase inhibitors, PPO inhibitors, PS II inhibitors, and synthetic auxins. Non-limiting examples of herbicides include acetochlor, clethodim, dicamba, flumioxazin, fomesafen, glyphosate, glufosinate, mesotrione, quizalofop, saflufenacil, sulcotrione, and 2,4-D.

Additional actives may also comprise substances such as, biological control agents, microbial extracts, plant growth activators or plant defense agents. Non-limiting examples of biological control agents include bacteria, fungi, beneficial nematodes, and viruses.

In certain embodiments, the biological control agent can be a bacterium of the genus *Actinomycetes, Agrobacterium, Arthrobacter, Alcaligenes, Aureobacterium, Azobacter, Beijerinckia, Brevibacillus, Burkholderia, Chromobacterium, Clostridium, Clavibacter, Comamonas, Corynebacterium, Curtobacterium, Enterobacter, Flavobacterium, Gluconobacter, Hydrogenophaga, Klebsiella, Methylobacterium, Paenibacillus, Pasteuria, Photorhabdus, Phyllobacterium, Pseudomonas, Rhizobium, Serratia, Sphingobacterium, Stenotrophomonas, Variovorax,* and *Xenorhabdus.*

In certain embodiments the biological control agent can be a fungus of the genus *Alternaria, Ampelomyces, Aspergillus, Aureobasidium, Beauveria, Colletotrichum, Coniothyrium, Gliocladium, Metarhizium, Muscodor, Paecilomyces, Trichoderma, Typhula, Ulocladium,* and *Verticillium.* In another embodiment the fungus is *Beauveria bassiana, Coniothyrium minitans, Gliocladium virens, Muscodor albus, Paecilomyces lilacinus,* or *Trichoderma polysporum.*

In further embodiments the biological control agents can be plant growth activators or plant defense agents including, but not limited to harpin, *Reynoutria sachalinensis,* jasmonate, lipochitooligosaccharides, and isoflavones.

In some embodiments, the nematicidal compositions described herein exhibit measurable nematode-killing activity or results in reduced fertility or sterility in the nematodes such that fewer viable or no offspring result, or compromise the ability of the nematode to infect or reproduce in its host, or interfere with the growth or development of a nematode. The nematicidal composition may also display nematode repellant properties.

For example, the nematicidal compositions described herein may reduce the survival time of adult nematodes relative to unexposed similarly staged adults, e.g., by about 20%, 40%, 60%, 80%, or more. In some embodiments, the nematicidal compositions described herein may cause the nematodes to cease replicating, regenerating, and/or producing viable progeny, e.g., by about 20%, 40%, 60%, 80%, or more. The effect may be apparent either immediately or in successive generations, or both.

The nematicidal compositions described herein can be used to treat diseases or infestations caused by nematodes of the following non-limiting, exemplary genera: *Globodera, Anguina, Ditylenchus, Tylenchorhynchus, Pratylenchus, Radopholus, Hirschmanniella, Nacobbus, Hoplolaimus, Scutellonema, Rotylenchus, Helicotylenchus, Rotylenchulus, Belonolaimus, Heterodera,* other cyst nematodes, *Meloidogyne, Criconemoides, Hemicycliophora, Paratylenchus, Tylenchulus, Aphelenchoides, Bursaphelenchus, Rhadinaphelenchus, Longidorus, Xiphinema, Trichodorus,* and *Paratrichodorus, Dirofilaria, Onchocerca, Brugia, Acanthocheilonema, Aelurostrongylus, Anchlostoma, Angiostrongylus, Ascaris, Bunostomum, Capillaria, Chabertia, Cooperia, Crenosoma, Dictyocaulus, Dioctophyme, Dipetalonema, Dracunculus, Enterobius, Filaroides, Haemonchus, Lagochilascaris, Loa, Manseonella, Muellerius, Necator, Nematodirus, Oesophagostomum, Ostertagia, Parafilaria, Parascaris, Physaloptera, Protostrongylus, Setaria, Spirocerca, Stephanogilaria, Strongyloides, Strongylus, Thelazia, Toxascaris, Toxocara, Trichinella, Trichostrongylus, Trichuris, Uncinaria,* and *Wuchereria.* In some embodiments, the nematicidal compositions described herein are used to treat diseases or infestations caused by nematodes including *Dirofilaria, Onchocerca, Brugia, Acanthocheilonema, Dipetalonema, Loa, Mansonella, Parafilaria, Setaria, Stephanofilaria, Wucheria, Pratylenchus, Heterodera, Meloidogyne,* and *Paratylenchus.* Examples of non-limiting species include: *Ancylostoma caninum, Haemonchus contortus, Trichinella spiralis, Trichurs muris, Dirofilaria immitis, Dirofilaria tenuis, Dirofilaria repens, Dirofilaria ursi, Ascaris suum, Toxocara canis, Toxocara cati, Strongyloides ratti, Parastrongyloides trichosuri, Heterodera glycines, Globodera pallida, Meloidogyne javanica, Meloidogyne incognita,* and *Meloidogyne arenaria, Radopholus similis, Longidorus elongatus, Meloidogyne hapla,* and *Pratylenchus penetrans.*

Having described the disclosure in detail, it will be apparent that modifications and variations are possible without departing from the scope of the claims.

EXAMPLES

The following non-limiting examples are provided for further illustration.

Example 1: Nematicidal Efficacy Assay

A miniaturized greenhouse assay was conducted to study the effects of several N-,C-disubstituted azole analogs on *Meloidogyne incognita* nematodes.

Cucumber seeds were sprouted for 3 days in moist paper towels. Acceptable sprouts were 3 to 4 cm long, with several lateral roots just emerging. For each trial compound, a stock solution was prepared in a mixture of acetone and TRITON X100 surfactant (412 mg in 500 mL), such that the concentration of the nematicidal test compound was 5 mg/mL. The chemical stock solution was then added to a mixture of deionized water (10 mL) and TRITON X100 (0.015% concentration), and mixed thoroughly to form the test solution.

Each test solution was evaluated in triplicate. Dry sand (10 mL) was added to each vial. Seedlings were planted by tilting the vial and laying the seedling in the correct orientation so that the cotyledons were just above the sand, and then tilting back to cover the radicles with sand.

A sample of the test solution (3.3 mL) was then added to each vial, and the vials were placed in racks under fluorescent light banks. The vials were inoculated two days after planting by adding 500 vermiform *M. incognita* eggs to each vial in deionized or spring water (50 µL). The vials were then kept under the fluorescent lamps at ambient room temperature and watered as needed with deionized water (1 mL), usually twice during duration of test.

Harvest of the cucumber plants was performed 10 to 12 days after inoculation by washing sand off the roots. A root gall rating was assigned using the following Gall rating scale (Gall: % root mass galled): 0=0-5%; 1=6-20%; 2=21-50%; and 3=51-100%. For each test solution, the average of the triplicate gall ratings was then calculated and scored: no galls=0.00-0.33; mild galling=0.67-1.33; moderate galling=1.67-2.33; severe galling=2.67-3.00.

The resulting nematicidal activity of the N—C-disubstituted azoles is set forth in Table 1A, below. Comparative solutions comprising other commercially available nematicidal compounds were also evaluated as controls, and are set forth in Table 1B.

TABLE 1A

Nematicidal activity of N-C-disubstituted azole analogs

| Name | Structure | Formula | 40/8/1 ppm gall ratings* |
|------|-----------|---------|--------------------------|
| 4-(furan-2-yl)-1-phenyl-1H-1,2,3-triazole | 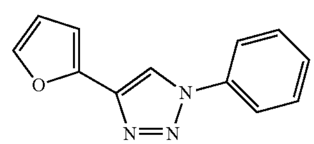 [SMILES: c1ccc(-n2cc(-c3ccco3)nn2)cc1] | Formula Ia-i | 0.00/1.33$^a$/2.67$^a$ |
| 1-phenyl-4-(thiophen-2-yl)-1H-pyrazole | 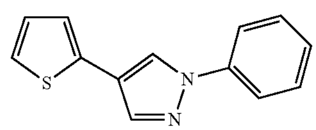 [SMILES: c1ccc(-n2cc(-c3cccs3)cn2)cc1] | Formula Ib-i | 0.00/0.33$^b$/3.00$^b$ |
| 1-(4-chlorophenyl)-4-(thiophen-2-yl)-1H-pyrazole | 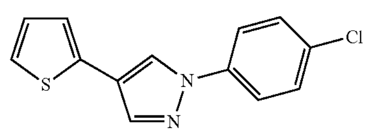 [SMILES: Clc1ccc(-n2cc(-c3cccs3)cn2)cc1] | Formula Ib-ii | 0.00/0.67$^b$/2.33$^b$ |
| 2-phenyl-4-(thiophen-2-yl)-2H-1,2,3-triazole | 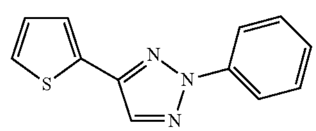 [SMILES: c1ccc(-n2ncc(-c3cccs3)n2)cc1] | Formula Id-i | 0.00/0.33$^a$/1.67$^a$ |
| 4-(furan-2-yl)-2-phenyl-2H-1,2,3-triazole | 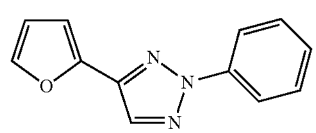 [SMILES: c1ccc(-n2ncc(-c3ccco3)n2)cc1] | Formula Id-ii | 0.00/1.00$^a$/2.33$^a$ |
| 4-(2,4-difluorophenyl)-1-(thiophen-2-yl)-1H-1,2,3-triazole | 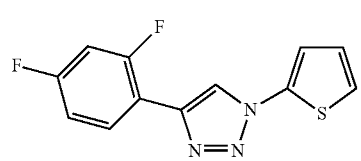 [SMILES: Fc1ccc(-c2cn(-c3cccs3)nn2)c(F)c1] | Formula IIa-i | 0.00/0.00$^c$/1.67$^c$ |
| 4-phenyl-1-(thiophen-2-yl)-1H-1,2,3-triazole | 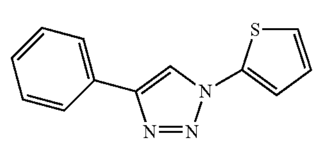 [SMILES: c1ccc(-c2cn(-c3ccco3)nn2)cc1] | Formula IIa-ii | 0.00/0.00$^a$/1.67$^a$ |

TABLE 1A-continued

Nematicidal activity of N-C-disubstituted azole analogs

| Name | Structure | Formula | 40/8/1 ppm gall ratings* |
|---|---|---|---|
| 1-(furan-2-yl)-4-phenyl-1H-1,2,3-triazole | 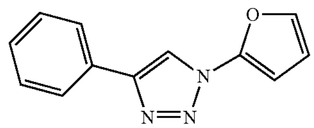 | Formula IIa-iii | 0.00/1.33$^a$/2.00$^a$ |
| 4-(4-chlorophenyl)-1-(thiophen-2-yl)-1H-imidazole | 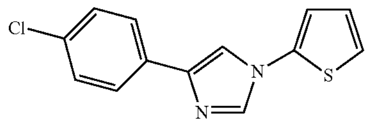 [SMILES: Clc1ccc(-c2cn(-c3cccs3)cn2)cc1] | Formula IIc-i | 0.00/1.33$^c$/1.67$^c$ |
| 1-(furan-2-yl)-4-phenyl-1H-imidazole | 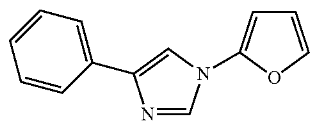 [SMILES: c1ccc(-c2cn(-c3ccco3)cn2)cc1] | Formula IIc-ii | 0.00/1.33$^c$/2.33$^c$ |
| 4-phenyl-1-(thiophen-2-yl)-1H-imidazole | 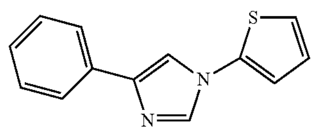 [SMILES: c1ccc(-c2cn(-c3cccs3)cn2)cc1] | Formula IIc-iii | 0.00/1.33$^b$/2.33$^b$ |
| 4-(furan-2-yl)-1-phenyl-1H-pyrazole | 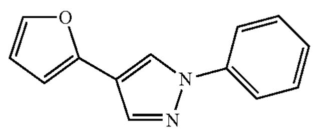 [SMILES: c1ccc(-n2cc(-c3ccco3)cn2)cc1] | Formula Ib-iii | 0.00/1.67/2.67 |
| 1-(4-chlorophenyl)-4-(furan-2-yl)-1H-imidazole | 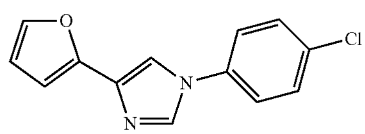 | Formula Ic-i | 0.33/2.00/3.00 |
| 1-(4-chlorophenyl)-4-(thiophen-2-yl)-1H-imidazole | 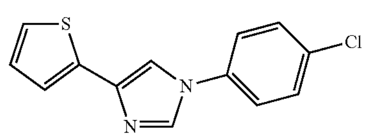 [SMILES: Clc1ccc(-n2cnc(-c3cccs3)c2)cc1] | Formula IIc-ii | 0.00/2.33/2.67 |
| 4-(4-chlorophenyl)-1-(furan-2-yl)-1H-imidazole | 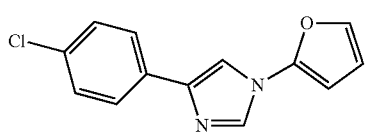 | Formula IIc-iv | 0.33/2.00/2.33 |
| 1-(2,4-difluorophenyl)-4-(thiophen-2-yl)-1H-1,2,3-triazole | 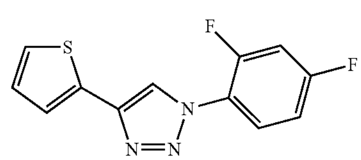 | Formula Ia-ii | 0.00/2.33/3.00 |
| 4-(4-fluorophenyl)-1-(thiophen-2-yl)-1H-1,2,3-triazole | 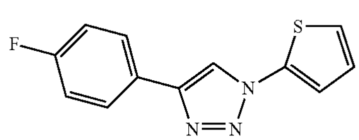 [SMILES: Fc1ccc(-c2cn(-c3cccs3)nn2)cc1] | Formula IIa-iv | 0.33/1.33/2.67 |
| 1-(4-chlorophenyl)-4-(furan-2-yl)-1H-1,2,3-triazole | 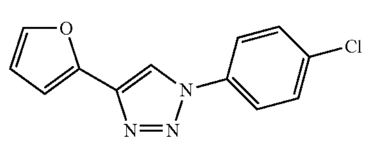 [SMILES: Clc1ccc(-n2cc(-c3ccco3)nn2)cc1] | Formula Ia-iiii | 0.00/1.00/2.67 |

TABLE 1A-continued

Nematicidal activity of N-C-disubstituted azole analogs

| Name | Structure | Formula | 40/8/1 ppm gall ratings* |
|---|---|---|---|
| 1-(4-fluorophenyl)-4-(furan-2-yl)-1H-1,2,3-triazole | 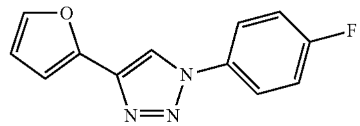 [SMILES: Fc1ccc(-n2cc(-c3ccco3)nn2)cc1] | Formula Ia-iv | 0.33/1.67/2.33 |
| 1-(2,4-difluorophenyl)-4-(furan-2-yl)-1H-1,2,3-triazole | 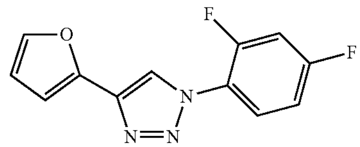 [SMILES: Fc1ccc(-n2cc(-c3ccco3)nn2)c(F)c1] | Formula Ia-v | 0.00/0.67/2.33 |
| 4-(4-chlorophenyl)-1-(furan-2-yl)-1H-1,2,3-triazole | 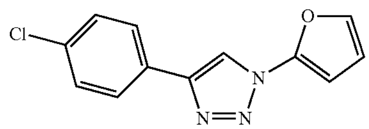 [SMILES: Clc1ccc(-c2cn(-c3ccco3)nn2)cc1] | Formula IIa-v | 0.00/0.67/2.33 |

*Data with the same letters are taken from the same test.

TABLE 1B

Nematicidal activity of comparative compositions

| Name | 40/8/1 ppm gall ratings* |
|---|---|
| Fenamiphos (1 ppm) | 0.00$^d$ |
| Vydate (1 ppm) | 1.0$^a$, 1.67$^b$, 1.33$^c$ |
| Abamectin (1 ppm) | 1.67$^d$ |

*Data with the same letters are taken from the same test.

Example 2: Description of Synthesis of the Compounds of Formula Ia

Generally, the compounds of the Formulas I, II, III and IV may be prepared using methods known to those skilled in the art.

For example, the compounds of Formula Ia can be prepared as set forth in Scheme 1 below. Generally, the 1,4-disubstituted triazoles of Formula Ia can be synthesized using a Sonogashira coupling-deprotection-click reaction sequence from aryl or heteroaryl halides, trimethylsilylacetylenes and organic azides (see generally Fiandanese et al., Synthesis, 2009, 22, 3853-3859 and Lorinca et al., Synthesis, 2009, 20, 3527-3532). The aryl azides are synthetically available from aryl halides under mild conditions (see generally Anderson et al., Synlett, 2005, 14, 2209-2213)

More particularly, as shown in Scheme 1, the heteroaryl halide 1 is reacted with the trimethylsilylacetylene 2, in the presence of palladium and copper catalysts, to form the intermediate 3. Intermediate 3 is then reacted with the aryl azide 4, in the presence of a catalyst, to form the 1,4-disubstituted triazole product 5.

In Scheme 1 below, substituent E may be selected as set forth with regard to Formula Ia above. In addition, the aryl and/or heteroaryl groups may be optionally independently substituted with substituents $R_1$ through $R_5$ and $R_7$ through $R_9$ as set forth with regard to Formula Ia above.

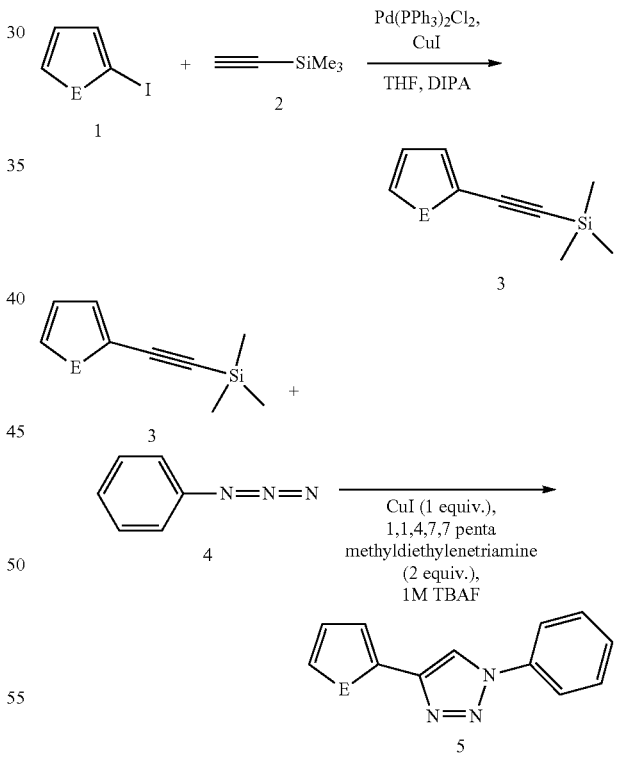

Scheme 1: Synthetic scheme for the preparation of compounds of Formula Ia

Example 3: Preparation of 4-(furan-2-yl)-1-phenyl-1H-1,2,3-triazole (Formula Ia-i)

A mixture of 2-bromofuran (500 mg, 3.402 mmol), Pd(PPh$_3$)$_2$Cl$_2$ (75.69 mg, 0.10784 mmol), CuI (40.17 mg, 0.2109 mmol) and diisopropylamine (0.89 ml, 6.395 mmol) in tetrahydrofuaran (THF) (4 ml) was degassed thoroughly with argon, and trimethylsilyl acetylene (0.648 ml, 4.694 mmol) was added at room temperature. After stirring the reaction mixture for 16 hours at room temperature, it was poured into water and extracted with dichloromethane. The combined organic layers were washed with brine and dried over anhydrous sodium sulfate and the solvent was evaporated. The crude material was purified by column chromatography (100-200 mesh silica gel) using hexane as eluent to yield the desired (furan-2-ylethynyl)trimethylsilane (200 mg, 1.21 mmol, yield 35.84%).

To a solution of furan-2-ylethynyl)trimethylsilane (100 mg, 0.6097 mmol), phenyl azide (0.5 M solution, 2.42 ml, 1.2195 mmol), and CuI (116.11 mg, 0.6097 mmol) in THF (2 ml) was added 1,1,4,7,7-pentamethyldiethlene triamine (0.254 ml, 1.2195 mmol) and 1M TBAF.3H$_2$O (1.20 ml, 1.2195 mmol). After stirring the reaction mixture for 20 hours at room temperature, it was quenched with saturated ammonium chloride solution and was extracted with ethyl acetate. The combined organic layers were washed with water, dried over anhydrous sodium sulfate and evaporated. The crude material was purified by column chromatography (100-200 mesh silica gel) using 5% ethyl acetate in hexane as eluent to yield 4-(furan-2-yl)-1-phenyl-1H-1,2,3-triazole (80 mg, 0.378 mmol, yield 62.18%) with an HPLC purity of 98.82%. LC-MS [M+H] 212 (C$_{12}$H$_9$N$_3$O+H expected 212.07), mp 118-120° C. The $^1$H-NMR spectra was in accordance with the chemical structure.

Example 4: Preparation of 1-phenyl-4-(thiophene-2-yl)-1H-1,2,3-triazole (Formula Ia-vi)

A mixture of 2-iodothiophene (500 mg, 2.38 mmol), Pd(PPh$_3$)$_2$Cl$_2$ (52.95 mg, 0.0754 mmol), CuI (28.1 mg, 0.14756 mmol) and diisopropylamine (0.62 ml, 4.4744 mmol) in THF (4 ml) was degassed thoroughly with argon, and trimethylsilyl acetylene (0.453 ml, 3.284 mmol) was added at room temperature. After stirring the reaction mixture for 16 hours at room temperature, it was poured into water and extracted with dichloromethane. The combined organic layers were washed with brine and dried over anhydrous sodium sulfate, and the solvent was evaporated. The crude material was purified by column chromatography (100-200 mesh silica gel) using hexane as eluent to yield 300 mg of trimethyl(thiophen-2-ylethynyl)silane (300 mg, 1.66 mol, yield 70.02%).

To a solution of trimethyl(thiophen-2-ylethynyl)silane (50 mg, 0.2777 mmol), phenyl azide (0.5 M solution, 1.1 ml, 0.555 mmol), and CuI (52.87 mg, 0.2777 mmol) in THF (1 ml) was added 1,1,4,7,7-pentamethyldiethlenetriamine (0.116 ml, 0.555 mmol) and 1M TBAF.3H$_2$O (0.554 ml, 0.554 mmol). After stirring the reaction mixture for 20 hours at room temperature, it was quenched with saturated ammonium chloride solution and was extracted with ethyl acetate. The combined organic layers were washed with water, dried over anhydrous sodium sulfate and evaporated. The crude material was purified by column chromatography (100-200 mesh silica gel) using 5% ethyl acetate in hexane as eluant to yield 1-phenyl-4-(thiophen-2-yl)-1H-1,2,3-triazole (30 mg, 0.132 mol, yield 47.61%) with an HPLC purity of 97.64%. LC-MS [M+H] 228.2 (C$_{12}$H$_9$N$_3$S+H, expected 228.05). The $^1$H-NMR spectra was in accordance with the chemical structure.

Example 5: Description of Synthesis of the Compounds of Formula Ia

The compounds of Formula Ia may be prepared as set forth in Scheme 2 below. Generally, the triazole ring may be formed via three-component coupling of aryl iodide, sodium azide, and terminal alkyne using a copper catalyst.

More particularly, as shown in Scheme 2, the heteroaryl alkyne 1 is reacted with the heteroaryl halide 2 and sodium azide 3, in the presence of a copper catalyst, to form the 1,4-disubstituted triazole product 5.

In Scheme 2 below, substituent E may be selected as set forth with regard to Formula Ia above. In addition, the aryl and/or heteroaryl groups may be optionally independently substituted with substituents R$_1$ through R$_5$ and R$_7$ through R$_9$ as set forth with regard to Formula Ia above.

Scheme 2: Synthetic scheme for the preparation of compounds of Formula Ia

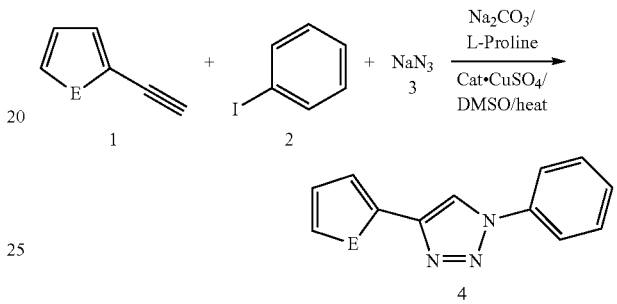

Example 6: Preparation of 1-(4-chlorophenyl)-4-(furan-2-yl)-1H-1,2,3-triazole (Formula Ia-iii)

A sealed tube was charged sequentially with 2-ethynylfuran (153 mg, 1.663 mmol), 1-chloro-4-iodobenzene (395 mg, 1.663 mmol), L-proline (38.2 mg, 0.332 mmol), Na$_2$CO$_3$ (35 mg, 0.332 mmol), sodium ascorbate (66 mg, 0.332 mmol), DMSO-H$_2$O (9:1; 7 ml), NaN$_3$ (130 mg, 1.99 mmol) and CuSO$_4$.5H$_2$O (415 mg, 1.663 mmol). The tube was sealed and stirred at 65° C. for 16 hours. The reaction mixture was poured onto cold ammonium hydroxide solution, and the mixture was extracted with ethyl acetate (3×30 ml). The combined organic layers were washed with brine solution (30 ml), dried over sodium sulfate and evaporated to yield the crude material, which was purified by column chromatography with 20% ethyl acetate/hexane yielding 1-(4-chlorophenyl)-4-(furan-2-yl)-1H-1,2,3-triazole (20 mg, yield 4.9%) as a pale yellow solid. The HPLC purity was 98.02%. LC-MS [M+H] 246 (C$_{12}$H$_8$ClN$_3$O+H, expected 246.04). The $^1$H-NMR spectra was in accordance with the chemical structure.

Example 7: Preparation of 1-(4-fluorophenyl)-4-(furan-2-yl)-1H-1,2,3-triazole (Formula Ia-iv)

The procedure described above in Example 6 for Formula Ia-iii was followed, starting from 2-ethynylfuran and 4-fluoro-1-iodobenzene, to prepare 1-(4-fluorophenyl)-4-(furan-2-yl)-1H-1,2,3-triazole as yellow solid (8 mg, mmol, yield 2.1%) with an HPLC purity of 98.32%. LC-MS [M+H] 230 (C$_{12}$H$_8$FN$_3$O+H, expected 230.07). The $^1$H-NMR spectra was in accordance with the chemical structure.

Example 8: Preparation of 1-(2,4-difluorophenyl)-4-(furan-2-yl)-1H-1,2,3-triazole (Formula Ia-v)

The procedure described above in Example 6 for Formula Ia-iii was followed, starting from 2-ethynylfuran and 2,4- difluoro-1-iodobenzene, to prepare 1-(2,4-difluorophenyl)-4-(furan-2-yl)-1H-1,2,3-triazole as yellow sticky solid (15.3 mg, 0.06 mmol, yield 2.0%) with an HPLC purity of 83.8%. LC-MS [M+H] 248 ($C_{12}H_7F_2N_3O$+H, expected 248.06). The $^1$H-NMR spectra was in accordance with the chemical structure.

Example 9: Preparation of 1-(4-chlorophenyl)-4-(thiophen-2-yl)-1H-1,2,3-triazole (Formula Ia-vii)

A sealed tube was sequentially charged with 2-ethynylthiophene (250 mg, 2.31 mol), 1-chloro-4-iodobenzene (551 mg, 2.31 mmol, 1.0 eq.), L-proline (53 mg, 0.462 mmol, 0.2 eq.), $Na_2CO_3$ (50 mg, 0.462 mmol, 0.2 eq.), sodium ascorbate (91 mg, 0.462 mmol, 0.2 eq.), and 4 mL of DMSO:$H_2O$ (9:1). Then $NaN_3$ (180 mg 2.77 mmol, 1.2 eq.) and $CuSO_4 \cdot 5H_2O$ (58 mg. 0.231 mmol, 0.1 eq.) were added, and the vessel was sealed. The suspension was stirred at 65° C. for 16 hours. The reaction mixture was then poured into ice-water and extracted with ethyl acetate. The organic layer was separated, washed with brine, dried over $Na_2SO_4$, and concentrated under vacuum. The crude product was then purified by silica column (100-200) using 15-20% ethyl acetate/hexanes to yield 1-(4-chloro-phenyl)-4-(thiophen-2-yl)-1H-1,2,3-triazole as a brown solid compound (34 mg, 0.13 mmol yield 5.5%). LC-MS [M+H] 261.8 ($C_{12}H_8ClN_3S$+H, expected 262.01). The $^1$H-NMR spectra was in accordance with the chemical structure.

Example 10: Preparation of 1-(2,4-difluorophenyl)-4-(thiophen-2-yl)-1H-1,2,3-triazole (Formula Ia-ii)

The procedure described above in Example 9 for Formula Ia-vii was followed starting from 2-ethynylthiophene (250 mg, 2.31 mmol) and 2,4-difluoro-1-iodobenzene (554 mg, 2.31 mmol, 1.0 eq,) to prepare 1-(2,4-difluorophenyl)-4-(thiophen-2-yl)-1H-1,2,3-triazole as a yellowish solid (34 mg, 0.129 mmol, yield 5.6%) with an HPLC purity of 93.63%. LC-MS [M+H] 264.2 ($C_{12}H_7F_2N_3S$+H, expected 264.03). The $^1$H-NMR spectra was in accordance with the chemical structure.

Example 11: Description of Synthesis of the Compounds of Formula Ib

The compounds of Formula Ib may be prepared as set forth in Scheme 3 below. Generally, the N-aryl substituted pyrazole 1 is reacted with boronic acid-substituted heteroaryl group 2, in the presence of a palladium catalyst, to form the 1,4-disubstituted pyrazole product 3.

In Scheme 3 below, substituent E may be selected as set forth with regard to Formula Ib above. In addition, the aryl and/or heteroaryl groups may be optionally independently substituted with substituents $R_1$ through $R_5$ and $R_7$ through $R_9$ as set forth with regard to Formula Ib above.

Scheme 3: Synthetic scheme for the preparation of compounds of Formula Ib

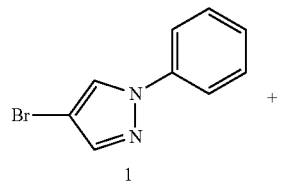

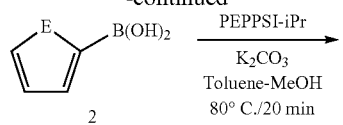

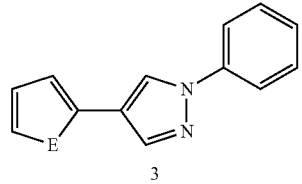

Example 12: Preparation of 1-phenyl-4-(thiophen-2-yl)-1H-pyrazole (Formula Ib-i)

4-Bromo-1-phenyl-1H-pyrazole (150 mg, 0.672 mmol), thiophen-2-ylboronic acid (296 mg, 2.31 mmol), PEPPSI-iPr (13.6 mg, 0.062 mmol), and $K_2CO_3$ (480 mg, 3.48 mmol) were combined in toluene-methanol (1:1) (2 ml). The reaction mixture was heated under microwave at 80° C. for 10 minutes. The reaction mixture was then filtered and washed with toluene-methanol (5 ml), and the filtrate was concentrated. The crude mixture was then column purified using 15-20% ethyl acetate/hexane to yield 1-phenyl-4-(thiophen-2-yl)-1H-pyrazole (42 mg, yield 27%). The HPLC purity of the final product was 99.32%. LC-MS [M+H] 227 ($C_{13}H_{10}N_2S$+H expected 227.06). The $^1$H-NMR spectra was in accordance with the chemical structure.

Example 13: Preparation of 1-(4-chlorophenyl)-4-(thiophen-2-yl)-1H-pyrazole (Formula Ib-ii)

The procedure described above in Example 12 for Formula Ib-i was followed, starting from 4-bromo-1-(4-chlorophenyl)-1H-pyrazole and thiophen-2-ylboronic acid, to prepare 1-(4-chlorophenyl)-4-(thiophen-2-yl)-1H-pyrazole 52 mg, mmol, yield 34%) after column purification with 20% ethyl acetate/hexanes. The HPLC purity of the final product was 99.43%. LC-MS [M+H] 261 ($C_{13}H_9ClN_2S$+H expected 261.02). The $^1$H-NMR spectra was in accordance with the chemical structure.

Example 14: Preparation of 4-(furan-2-yl)-1-phenyl-1H-pyrazole (Formula Ib-iii)

4-bromo-1-phenyl-1H-pyrazole (140 mg, 0.627 mmol), furan-2-ylboronic acid (88.2 mg, 0.941 mmol), $Pd(PPh_3)_4$ (70 mg, 0.062 mmol), and $Cs_2CO_3$ (400 mg, 1.254 mmol) were combined in toluene-methanol (1:1) (2 ml). The reaction mixture was heated under microwave at 80° C. for 60 minutes. The reaction mixture was then filtered and washed with toluene-ethanol (5 ml), and the filtrate was concentrated. The crude product was column purified using 15-20% ethyl acetate/hexanes, and was then further purified by preparative HPLC to yield the desired 4-(furan-2-yl)-1-phenyl-1H-pyrazole (22 mg, 0.10 mmol 16.7%). The HPLC purity of the final product was 99.72%. LC-MS [M+H] 211 ($C_{13}H_{10}N_2O$+H expected 211.08). The $^1$H-NMR spectra was in accordance with the chemical structure.

Example 15: Description of Synthesis of the Compounds of Formula Ic

The compounds of Formula Ic may be prepared as set forth in Scheme 4 below. Generally, the boronic acid-substituted aryl 1 is reacted with the 4-halogenated imidazole 2, in the presence of a copper catalyst, to form the N-aryl substituted imidazole 3. The N-aryl substituted imidazole 3 is then reacted with a boronic acid-substituted heteroaryl 5, in the presence of a palladium catalyst, to form the 1,4-disubstituted imidazole product 5.

In Scheme 4 below, substituent E may be selected as set forth with regard to Formula Ic above. In addition, the aryl and/or heteroaryl groups may be optionally independently substituted with substituents $R_1$, through $R_5$ and $R_7$ through $R_9$ as set forth with regard to Formula Ic above.

Scheme 4: Synthetic scheme for the preparation of compounds of Formula Ic

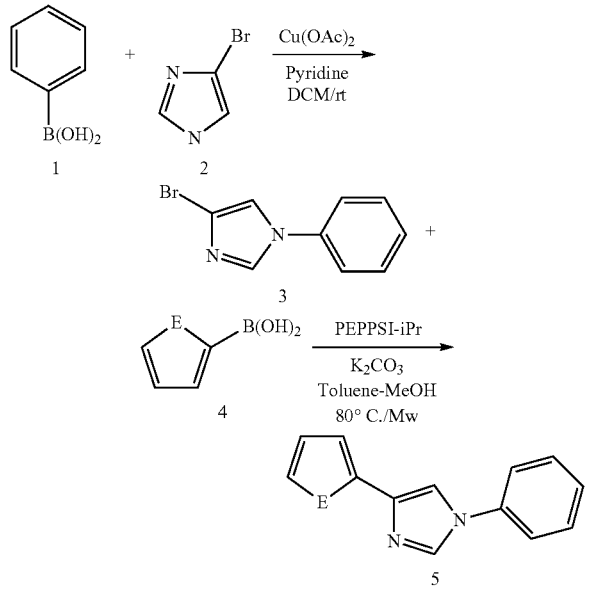

Example 16: Preparation of 4-(furan-2-yl)-1-phenyl-1H-imidazole (Formula Ic-iii)

4-Bromo-1H-imidazole (500 mg, 3.4 mmol, 1 eq), phenylboronic acid (830 mg, 6.8 mmol, 2 eq), anhydrous cupric acetate (926 mg, 5.1 mmol), activated 4 Å molecular sieves (2 g) and pyridine (0.3 ml) were combined in dichloromethane (20 ml) and stirred for 2 days in the presence of air. The reaction mass was then filtered through Celite, washed with methanol, and concentrated and purified by silica gel chromatography (eluent 15% ethyl acetate/hexane) to afforded yellowish sticky solid 4-bromo-1-phenyl-1H-imidazole (200 mg, 26%).

4-Bromo-1-phenyl-1H-imidazole (200 mg, 0.9 mmol), furan-2-ylboronic acid (342 mg, 3 mmol), PEPPSI-iPr (18 mg, 0.026 mmol), and $K_2CO_3$ (640 mg, 4.64 mmol) were then combined in toluene-methanol (1:1) (4 ml). The reaction mixture was heated under microwave at 80° C. for 20 minutes. It was then filtered and washed with toluene-MeOH (5 ml), and the filtrate was concentrated to yield a crude mixture. The crude mixture was then column purified using 15-20% ethyl acetate/hexanes to afford the desired 4-(furan-2-yl)-1-phenyl-1H-imidazole (50 mg, 0.19 mmol, yield 21.4%) as a brown sticky liquid with an HPLC purity of 95.5%. LC-MS [M+H] 211 ($C_{13}H_{10}N_2O$+H expected 211.08). The $^1$H-NMR spectra was in accordance with the chemical structure.

Example 17: Preparation of 1-(4-chlorophenyl)-4-(furan-2-yl)-1H-imidazole (Formula Ic-i)

The procedure described above for Formula Ic-iii in Example 16 was followed, starting from 4-chloro-phenylboronic acid and 4-bromo-1H-imidazole, to prepare 4-bromo-1-(4-chlorophenyl)-1H-imidazole, which was then reacted with furan-2-ylboronic acid to prepare the desired 1-(4-chlorophenyl)-4-(furan-2-yl)-1H-imidazole (15 mg, 0.061 mmol, yield 12%) as an off-white solid. The HPLC purity of the final product was 95.45%. LC-MS [M+H] 245 ($C_{13}H_9ClN_2O$+H expected 245.04). The $^1$H-NMR spectra was in accordance with the chemical structure.

Example 18: Preparation of 1-(4-chlorophenyl)-4-(thiophen-2-yl)-M-imidazole (Formula Ic-ii)

The procedure described above for Formula Ic-iii in Example 16 was followed, starting from 4-chloro-phenylboronic acid and 4-bromo-1H-imidazole, to prepare 4-bromo-1-(4-chlorophenyl)-1H-imidazole. 4-Bromo-1-(4-chlorophenyl)-1H-imidazole (150 mg, 0. 0.583 mmol), thiophen-2-ylboronic acid (149 mg, 1.66 mmol), $Pd_2(dba)_3$ (27 mg, 0.029 mmol), 2-Dicyclohexylphosphino-2',4',6'-triisopropylbiphenyl (XPhos) (28 mg, 0.058 mmol) and $Cs_2CO_3$ (475 mg. 1.459 mmol) were then combined in dioxane (5 ml). The reaction mixture was heated under microwave at 90° C. for 16 hours. It was then filtered and washed with ethyl acetate, and the filtrate was concentrated. The crude material was column purified using 15-20% ethyl acetate/hexanes to yield the desired 1-(4-chlorophenyl)-4-(thiophen-2-yl)-1H-imidazole (16 mg, 0.061 mmol, yield 10%) as a reddish solid. The HPLC purity of the final product was 99.35%. LC-MS [M+H] 261 ($C_{13}H_9ClN_2S$+H expected 261.02). The $^1$H-NMR spectra was in accordance with the chemical structure

Example 19: Description of Synthesis of the Compounds of Formula Id

The compounds of Formula Id may be prepared as set forth in Scheme 5 below. Generally, the heteroaryl carboxylate 1 is reacted with cobalt(II) chloride to form the heteroaryl acyl chloride 2, which is then reacted with diazomethane to form the intermediate diazo compound 3. The diazo intermediate 3 is then reacted with the 3,4,5,6-tetrachlorocyclohexa-3,5-diene-1,2-dione 4 to produce the intermediate 5, which is then reacted with phenylhydrazine to form the heteroaryl-substituted diphenylhydrazine intermediate 6. Intermediate 6 is then refluxed in the presence of a copper catalyst to form the 2-aryl-4-heteroaryl-1,2,3-triazole product 7.

In Scheme 5 below, substituent E may be selected as set forth with regard to Formula Id above. In addition, the aryl and/or heteroaryl groups may be optionally independently substituted with substituents $R_1$ through $R_5$ and $R_7$ through $R_9$ as set forth with regard to Formula Id above.

Scheme 5: Synthetic scheme for the preparation of compounds of Formula Id

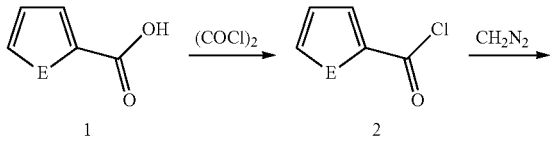

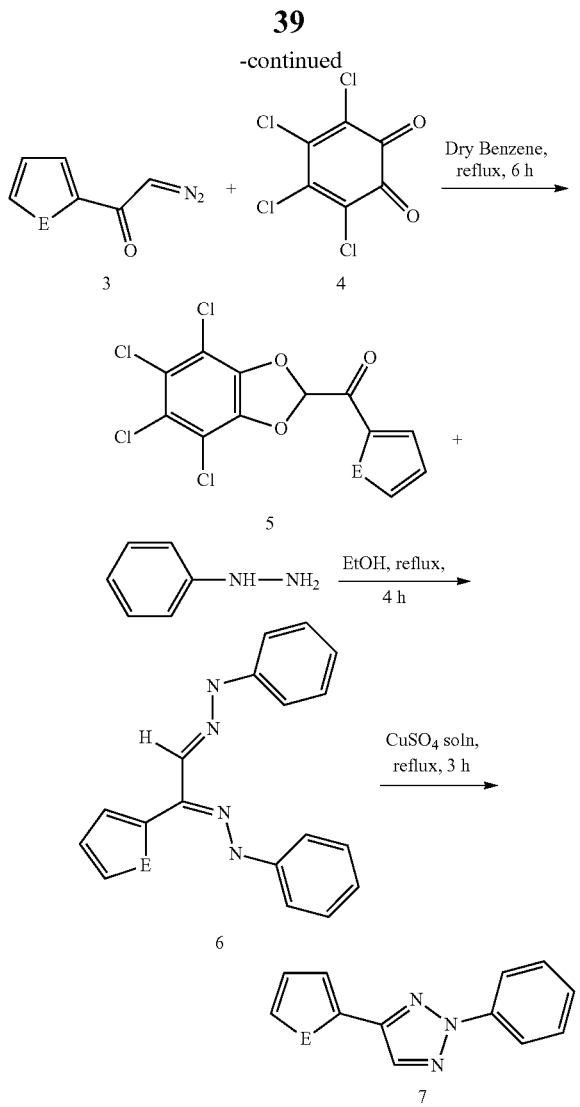

Example 20: Preparation of 2-phenyl-4-(thiophen-2-yl)-2H-1,2,3-triazole (Formula Id-i)

To an ice-cooled and stirred suspension of thiophene-2-carboxylic acid (5 g, 39.01 mmol) in dry dichloromethane (50 mL) was added oxalyl chloride (17.6 mL, 185.12 mmol) followed by 2-3 drops of dry N,N-dimethylformamide (DMF). Effervescence occurred. The reaction was allowed to warm to room temperature, and was then stirred for 3-4 hours at room temperature, during which the solution became clear. After completion of the reaction (as indicated by thin layer chromatography), the solvent was evaporated to dryness (keeping water bath temperature bellow 40° C.) to yield crude thiophene-2-carbonyl chloride (5.7 g, 99%) as a yellow liquid.

Thiophene-2-carbonyl chloride (5.7 g, 38.88 mmol) was combined with dry ether (200 mL) and cooled in an ice bath. N-Nitroso-N-methylurea (102 g, 989.52 mmol) was treated with a concentrated aqueous NaOH solution, in an ice cold condition in a conical flask, to produce diazomethane. The diazomethane was then combined with dry ether (100 mL), dried over KOH, and added to the reaction mass at 0° C. Diazomethane produced similarly as above was added to the reaction mass twice. Reaction was allowed to stir overnight at RT. The solvent was evaporated to dryness, and the crude product was purified by column chromatography using 100-200 mesh silica gel and 20% ethyl acetate in hexane as solvent system, which yielded 2-diazo-1-(thiophen-2-yl)ethanone (2.5 g, 42%) as a yellow solid.

2-diazo-1-(thiophen-2-yl)ethanone (2.3 g, 0.0151 mol) and 3,4,5,6-tetrachlorocyclohexa-3,5-diene-1,2-dione (3.36 g, 0.0136 mol) were then combined in dry benzene (25 mL) and refluxed vigorously for 6 hours. The solvent was then evaporated to dryness, and the crude material was subjected to column chromatography using 100-200 mesh silica gel and 15% ethyl acetate-hexane solvent system. Evaporation of the solvent yielded (4,5,6,7-tetrachlorobenzo[d][1,3]dioxol-2-yl)(thiophen-2-yl)methanone as an orange solid (2.2 g, 43.4%).

A mixture of (4,5,6,7-tetrachlorobenzo[d][1,3]dioxol-2-yl)(thiophen-2-yl)methanone (1 g, 2.70 mmol) and phenyl hydrazine (880 mg, 8.13 mmol) in ethanol (14 mL) was heated under reflux for 30 minutes. The reaction mixture was then cooled in an ice bath. A solid precipitated, and the precipitate was collected by filtration and washed with hexane. Crude 2,2'-(1-(thiophen-2-yl)ethane-1,2-diylidene)bis(1-phenylhydrazine) was obtained as a brown solid (500 mg, 57.8% yield) and used in the next step without further purification.

An aqueous solution of hydrated copper sulphate (532 g, 2.13 mmol) in 4 mL of demineralized water was added portion-wise to a solution of 2,2'-(1-(thiophen-2-yl)ethane-1,2-diylidene)bis(1-phenylhydrazine (200 mg, 0.624 mmol) in dioxane (5 mL) while heating under reflux. After complete addition heating was continued further for 3 hours. The reaction mixture was filtered while hot, left to cool, and extracted with ether. The ethereal extract was dried ($Na_2SO_4$), filtered, and evaporated to dryness. Column purification of the crude compound, using 100-200 mesh range silica gel and ethyl acetate-hexane solvent system, furnished the desired 2-phenyl-4-(thiophen-2-yl)-2H-1,2,3-triazole as a brown solid. The final product was further purified by washing with hexane. The yield of the final product was 36 mg (25.7%). The HPLC purity of the final product was 98.72%. The final product was observed to have a melting point of 78° C. LC-MS (M+1) 228 ($C_{12}H_9N_3S$+H expected 228.05). The $^1$H-NMR spectra was in accordance with the chemical structure.

Example 21: Preparation of 4-(furan-2-yl)-2-phenyl-2H-1,2,3-triazole (Formula Id-ii)

Furan-2-carboxylic acid (3 g, 26.76 mmol) was suspended in 30 ml of dry dichloromethane and cooled in an ice bath. Oxalyl chloride (12.2 ml, 133.82 mmol) was added to the reaction mass, followed by 2-3 drops of dry DMF. Effervescence occurred. The reaction mixture was allowed to warm to room temperature, and was stirred for 3-4 hours at room temperature, during which the solution became clear. Upon completion of the reaction, as indicated by thin layer chromatography, solvents were evaporated to dryness (keeping the water bath temperature below 25° C.). Crude furan-2-carbonyl chloride was obtained as a yellow liquid (3.45 g, 99%) and was used without further processing in the next step.

N-Nitroso-N-methylurea (16.14 g, 61.53 mmol) was treated with a concentrated NaOH aqueous solution to produce diazomethane. The diazomethane was combined with dry ether (100 ml), dried over KOH, and the resulting ethereal solution was cooled in an ice-salt bath. A solution of furan-2-carbonyl chloride (1.6 g, 12.3 mmol) in dry ether (25 ml) was then added very slowly to the diazomethane solution. The reaction mixture was stirred overnight at room temperature. The solvent was evaporated to dryness (under an argon atmosphere, and keeping the water bath temperature below 25° C.), and the resulting crude material was purified by column chromatography using 230-400 mesh silica gel and 1% triethylamine in DCM solvent system. Evaporation of solvent yielded 2-diazo-1-(furan-2-yl)ethanone as a yellow oil (900 mg, 49%).

2-diazo-1-(furan-2-yl)ethanone (900 mg, 6.61 mmol) and 3,4,5,6-tetrachlorocyclohexa-3,5-diene-1,2-dione (846 mg, 10.05 mmol) were combined in dry benzene (10 ml) and refluxed vigorously for 6 hours. The solvent was evaporated to dryness, and the resulting crude material was subjected to column chromatography using 100-200 mesh range silica gel and an ethyl acetate/hexane solvent system. The crude material was a mixture of two compounds, which were separated by column chromatography. Crystallization from acetone yielded furan-2-yl(4,5,6,7-tetrachlorobenzo[d][1,3] dioxol-2-yl)methanone as a yellow solid (200 mg, 16.4%).

A mixture of furan-2-yl(4,5,6,7-tetrachlorobenzo[d][1,3] dioxol-2-yl)methanone (200 mg, 0.568 mmol) and phenylhydrazine (185 mg, 1.704 mmol) in ethanol (3 ml) was heated under reflux for 30 minutes. During the course of the reflux, a yellow solid initially precipitated, but then dissolved upon further heating. The solvent was evaporated to dryness, and the resulting crude material was subjected to flash column chromatography using 7% ethyl acetate/hexane as an eluent to yield (2E)-2,2'-(1-(furan-2-yl)ethane-1,2-diylidene)bis(1-phenylhydrazine) as a yellow solid (150 mg, 87%).

An aqueous solution of hydrated copper sulphate (421 mg, 1.68 mmol) in 2 mL of demineralized water was added portion-wise to a solution of (2E)-2,2'-(1-(furan-2-yl)ethane-1,2-diylidene)bis(1-phenylhydrazine) (150 mg, 0.493 mmol) in dioxane (3.3 ml) while heating under reflux. After complete addition, heating was continued further for 2 hours. The solvent was then evaporated to dryness. The resulting crude material was subjected to flash column chromatography using an ethyl acetate/hexane solvent system (1-1.5%) to yield the desired compound 4-(furan-2-yl)-2-phenyl-2H-1,2,3-triazole as a yellow solid (60 mg, 57.7%). The HPLC purity of the final product was 96.03%. LC-MS[M+1] ($C_{12}H_9N_3O$+H expected 212.07). The melting point of the final compound was observed to be 80° C. The $^1$H NMR spectra was in accordance with the chemical structure.

Example 22: Description of Synthesis of the Compounds of Formula IIa

The compounds of Formula IIa may be prepared as set forth in Scheme 6 below. Generally, the 2-halogenated heteroaryl 1 is reacted with ethynylbenzene 2, sodium azide, and L-proline 3, in the presence of a copper catalyst, to form the 1,4-disubstituted 1,2,3-triazole product 4.

In Scheme 6 below, X represents a halogen atom, most typically I or Br. Substituent E may be selected as set forth with regard to Formula IIa above. In addition, the aryl and/or heteroaryl groups may be optionally independently substituted with substituents $R_1$ through $R_5$ and $R_7$ through $R_9$ as set forth with regard to Formula IIa above.

Scheme 6: Synthetic scheme for the preparation of compounds of Formula IIa

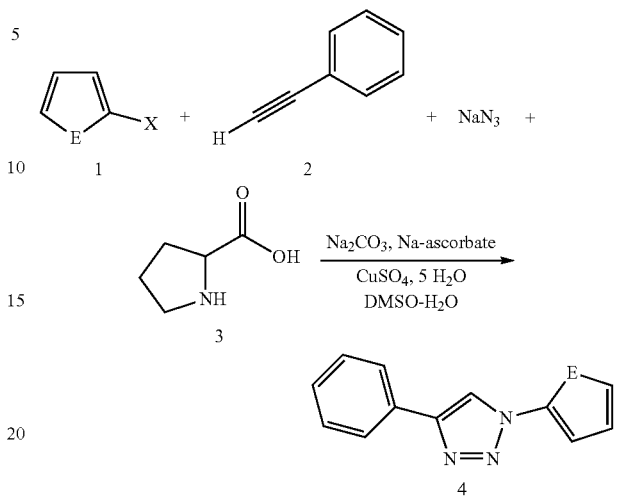

Example 23: Preparation of 4-(4-chlorophenyl)-1-(furan-2-yl)-1H-1,2,3-triazole (Formula IIa-v)

A sealed tube was charged sequentially with 2-iodofuran (400 mg, 2.061 mmol), 1-chloro-4-ethynylbenzene (280 mg, 2.061 mmol), L-proline (47.4 mg, 0.412 mmol), $Na_2CO_3$ (44 mg, 0.412 mmol), sodium ascorbate (82 mg, 0.412 mmol), DMSO-$H_2O$ (9:1; 9 ml), $NaN_3$ (160 mg, 2.47 mmol) and $CuSO_4 \cdot 5H_2O$ (514 mg, 2.061 mmol). The tube was sealed and stirred at 65° C. for 16 hours. The reaction mixture was then poured into a cold ammonium hydroxide solution, and the mixture was extracted with ethyl acetate (3×30 ml). The combined organic layers were washed with brine solution (30 ml), dried over sodium sulfate, and evaporated to yield the crude product, which was purified by column chromatography with 20% ethyl acetate/hexane to yield 4-(4-chlorophenyl)-1-(furan-2-yl)-1H-1,2,3-triazole (6 mg, 1.2%) as a pale yellow solid. The HPLC purity of the final product was 93.6%. LC-MS[M+1] 246 ($C_{12}H_8ClN_3O$+H expected 246.04). The $^1$H-NMR spectra was in accordance with the chemical structure.

Example 24: Preparation of 1-(furan-2-yl)-4-phenyl-1H-1,2,3-triazole (Formula IIa-iii)

A stirred solution of 2-bromofuran (500 mg, 3.40 mmol) and phenyl acetylene (347 mg, 3.39 mmol) in a mixture of solvents (9:1 DMSO:$H_2O$, 4 mL) was prepared in a Pierce reaction vessel. L-proline (78 mg, 0.68 mmol), sodium carbonate (72 mg, 0.68 mmol), sodium azide (265 mg, 4.07 mmol), copper sulfate, pentahydrate (43 mg, 0.17 mmol), and sodium ascorbate (67 mg, 0.34 mmol), respectively, were then added to the vessel. The reaction vessel was capped and the mixture was heated at 65° C. for 18 hours. The reaction mass was poured into 50 mL of ice-water, stirred for 10 minutes, and extracted with ethyl acetate (3×30 mL). The combined organic extract was then washed with brine (50 mL), dried over $Na_2SO_4$, and evaporated under vacuum. The resulting crude compound was auto purified through preparative HPLC to yield the desired 1-(furan-2-yl)-4-phenyl-1H-1,2,3-triazole (36 mg, 5%) as a light yellow solid. The melting point of the final product was determined to be 99-101° C. The HPLC purity of the final product was 95.34%. LC-MS [M+1] 212 ($C_{12}H_9N_3O$+H expected 212.07). The $^1$H-NMR spectra was in accordance with the chemical structure.

Example 25: Preparation of 4-(2,4-difluorophenyl)-1-(thiophen-2-yl)-1H-1,2,3,-triazole (Formula IIa-i)

The procedure described above in Example 23 for Formula IIa-v was followed, starting from 1-ethynyl-2,4-difluorobenzene (250 mg, 1.81 mmol) and 2-iodothiophene, to prepare 4-(2,4-difluorophenyl)-1-(thiophen-2-yl)-1H-1,2,3-triazole (12 mg, 0.046 mmol, yield 2.5%) as an off-white solid. The HPLC purity of the final product was 99.31%. LC-MS [M+H] 264 ($C_{12}H_7F_2N_3S$+H expected 264.03). The $^1$H-NMIR spectra was in accordance with the chemical structure.

Example 26: Description of Synthesis of the Compounds of Formula IIa

The compounds of Formula IIa may be prepared as set forth in Scheme 7 below. Generally, 4-methylbenzenesulfonic acid 1 is reacted with the heteroaryl 2 in the presence of iodine and meta-Chloroperoxybenzoic acid (m-CPBA) to form intermediate 3. Intermediate 3 is then reacted with ethynylbenzene 4 and sodium azide, in the presence of a copper catalyst, to form the 1,4-disubstituted 1,2,3-triazole product 5.

In Scheme 7 below, substituent E may be selected as set forth with regard to Formula IIa above. In addition, the aryl and/or heteroaryl groups may be optionally independently substituted with substituents $R_1$ through $R_5$ and $R_7$ through $R_9$ as set forth with regard to Formula IIa above.

Scheme 7: Synthetic scheme for the preparation of compounds of Formula IIa

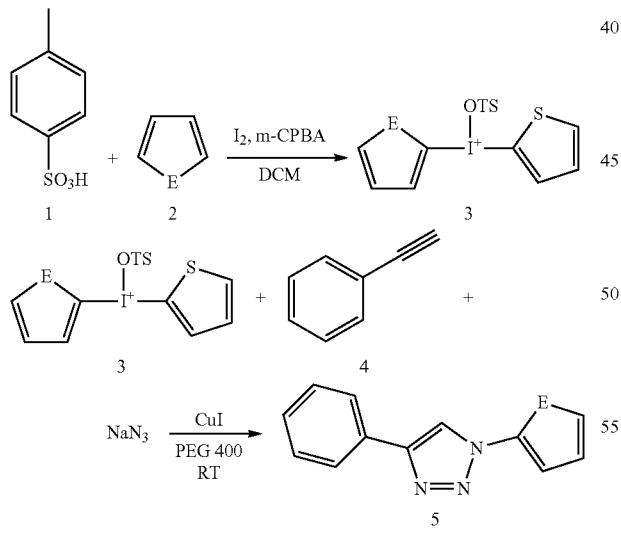

Example 27: Preparation of 4-phenyl-1-(thiophen-2-yl)-1H-1,2,3-triazole (Formula IIa-ii)

Iodine (862 mg, 3.39 mmol), m-CPBA (1.48 g, 8.62 mmol) and thiophene (1 g. 11.88 mmol) were combined in dry dichloromethane (66 mL). p-Toluene sulfonic acid (2.19 g, 11.56 mmol) was added to the solution at room temperature, and the mixture was stirred for 16 hours at room temperature. The solution was evaporated to dryness, and the resulting crude product was subjected to flash chromatography (5-10% MeOH/$CH_2Cl_2$)) to yield dithienyliodonium tosylate (11.2%) as a brown colored sticky mass.

A mixture of dithienyliodonium tosylate (200 mg, 0.446 mmol), $NaN_3$ (29 mg, 0.446 mmol), and copper (I) iodide (9 mg, 0.446 mmol) in a mixture of PEG 300 and $H_2O$ (0.5 mL, 1:1, v/v) was stirred at room temperature for 30 minutes. Phenyl acetylene (0.05 mL, 0.446 mmol) was added, and the reaction mixture was stirred for a further 30 minutes at room temperature. Upon completion of reaction as indicated by thin layer chromatography, the product was extracted with ether (3×5 mL). The organic layer was dried over anhydrous $Na_2SO_4$ and evaporated. Flash column chromatography of the crude product was done (5-10% ethyl acetate/hexane) to yield 4-phenyl-1-(thiophen-2-yl)-1H-1,2,3-triazole (29 mg, 28%) as an off-white crystalline solid. The melting point of the final product was determined to be 139-141° C. The HPLC purity of the final product was 91.11%. LC-MS [M+H] 228 ($C_{12}H_9N_3S$+H expected 228.05). The $^1$H-NMR spectra was in accordance with the chemical structure.

Example 28: Description of Synthesis of the Compounds of Formula IIc

The compounds of Formula IIc may be prepared as set forth in Scheme 8 below. Generally, the 4-phenyl-1H-imidazole 1 is reacted with the 2-halogenated heteroaryl 2, in the presence of a copper catalyst and trans-N,N' dimethylcyclohexane diamine, to form the 1,4-disubstituted imidazole product 3.

In Scheme 8 below, substituent E may be selected as set forth with regard to Formula IIc above. In addition, the aryl and/or heteroaryl groups may be optionally independently substituted with substituents $R_1$ through $R_5$ and $R_7$ through $R_9$ as set forth with regard to Formula IIc above.

Scheme 8: Synthetic scheme for the preparation of compounds of Formula IIc

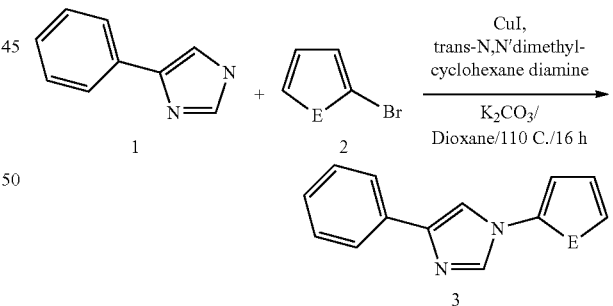

Example 29: Preparation of 4-phenyl-1-(thiophen-2-yl)-1H-imidazole (Formula IIc-iii)

A suspension of 4-phenyl-1H-imidazole (500 mg, 3.47 mmol), 2-bromothiophene (0.4 ml, 4.16 mmol), CuI (131.9 mg, 0.694 mmol, trans-N,N'-dimethylcyclohexanediamine (0.08 ml, 0.694 mmol), and $K_2CO_3$ (1.43 g, 10.4 mmol) in dioxane (5 ml) was heated at 110° C. in a sealed tube for 16 hours. The reaction mixture was then diluted with ethyl acetate and filtered. The filtrate was concentrated and purified by column chromatography using 15-20% ethyl acetate/hexanes to yield the desired 4-phenyl-1-(thiophen-2-yl)-1H-imidazole (23 mg, 3%). The HPLC purity of the final product was 99.7%. LC-MS [M+H] 227 ($C_{13}H_{10}N_2S$+H expected 227.06).

Example 30: Preparation of 1-(furan-2-yl)-4-phenyl-1H-imidazole (Formula IIc-ii)

The procedure described above in Example 29 for Formula IIc-iii was followed, starting from 4-phenyl-1H-imidazole (250 mg, 1.73 mmol) and 2-bromofuran, to prepare the desired 1-(furan-2-yl)-4-phenyl-1H-imidazole (27 mg, 0.13 mmol, yield 7.4%) as a brownish solid. The HPLC purity of the final product was 99.8%. LC-MS [M+H] 211 ($C_{13}H_{10}N_2O$+H expected 211.08). The $^1$H-NMR spectra was in accordance with the chemical structure.

Example 31: Preparation of 4-(4-chlorophenyl)-1-(furan-2-yl)-M-imidazole (Formula IIc-iv)

The procedure described above in Example 29 for Formula IIc-iii was followed, starting from 4-(4-chlorophenyl)-1H-imidazole (125 mg, 0.7 mmol) and 2-bromofuran, to prepare the desired 4-(4-chlorophenyl)-1-(furan-2-yl)-1H-imidazole (3 mg, 0.12, yield 1.7%) as a brownish solid. The HPLC purity of the final product was 95.84%. LC-MS [M+H] 245 ($C_{13}H_9ClN_2O$+H expected 245.04). The $^1$H-NMR spectra was in accordance with the chemical structure.

Example 32: Preparation of 4-(4-chlorophenyl)-1-(thiophen-2-yl)-1H-imidazole (Formula IIc-i)

The procedure described above in Example 29 for Formula IIc-iii was followed, starting from 4-(4-chlorophenyl)-1H-imidazole (125 mg, 0.595 mmol) and 2-bromothiophene, to prepare the desired 4-(4-chlorophenyl)-1-(thiophen-2-yl)-1H-imidazole (11 mg, 0.042 mmol, yield 7.0%) as a reddish sticky solid. The HPLC purity of the final product was 95.62%. LC-MS [M+H] 261 ($C_{13}H_9ClN_2S$+1 expected 261.02). The $^1$H-NMR spectra was in accordance with the chemical structure.

When introducing elements herein, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A compound of Formula I or a salt thereof,

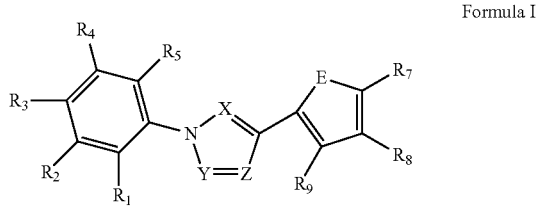

Formula I wherein $R_1$ and $R_5$ are independently selected from the group consisting of hydrogen, halogen, $CH_3$, $CF_3$, and $OCF_3$;

$R_2$ and $R_4$ are independently selected from the group consisting of hydrogen, halogen, and $CF_3$;

$R_3$ is selected from the group consisting of hydrogen, halogen, $CH_3$, $CF_3$, $OCF_3$, $OCH_3$, CN, and C(H)O;

$R_7$, $R_8$ and $R_9$ are independently selected from the group consisting of hydrogen, halogen, $CH_3$, and $OCF_3$;

X is N or C;

Y is N or C;

and Z is N or C, with the proviso that at least one of X, Y, and Z is C; and

E is selected from the group consisting of O, S, and N—$R_{10}$, wherein $R_{10}$ is alkyl;

provided that:

when X is C, Y is N, Z is N, and E is S, at least one of $R_1$ through $R_5$ and $R_7$ through $R_9$ is other than hydrogen;

when X is C, Y is N, Z is C, E is S, and $R_1$, $R_2$, $R_4$, $R_5$, and $R_7$ through $R_9$ are each hydrogen, $R_3$ is other than F;

when X is N, Y is N, Z is C, and E is O or S, at least one of $R_1$ through $R_5$ and $R_7$ through $R_9$ is other than hydrogen;

when X is N, Y is C, Z is N, and E is S, at least one of $R_1$, $R_2$, $R_4$, $R_5$, and $R_7$ through $R_9$ is other than hydrogen or $R_1$, $R_2$, $R_4$, $R_5$, and $R_7$ through $R_9$ are hydrogen and $R_3$ is other than hydrogen or $CH_3$;

when X is N, Y is C, Z is C, and E is S, at least one of $R_1$, $R_2$, $R_4$, $R_5$, and $R_7$ through $R_9$ is other than hydrogen or $R_1$, $R_2$, $R_4$, $R_5$, and $R_7$ through $R_9$ are hydrogen and $R_3$ is other than hydrogen, Br or $OCH_3$; and when X is N, Y is C, Z is C, E is O or N—$R_{10}$ and $R_1$, $R_2$, $R_4$, $R_5$, and $R_7$ through $R_9$ are hydrogen, $R_3$ is other than $OCH_3$.

2. The compound of claim 1 wherein the compound is of Formula Ia or a salt thereof,

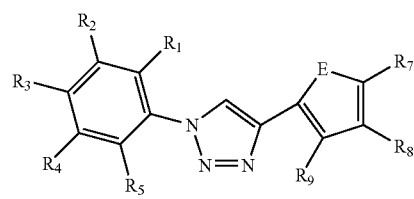

Formula Ia wherein $R_1$ and $R_5$ are independently selected from the group consisting of hydrogen, $CH_3$, F, Cl, Br, $CF_3$, and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_7$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl;

with the proviso that when E is S, at least one of $R_1$ through $R_5$ and $R_7$ through $R_9$ is other than hydrogen.

3. The compound of claim 1 wherein the compound is of Formula Ib or a salt thereof,

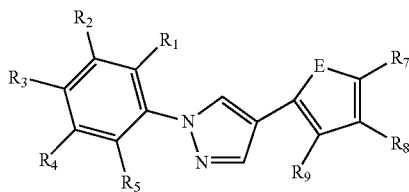
Formula Ib

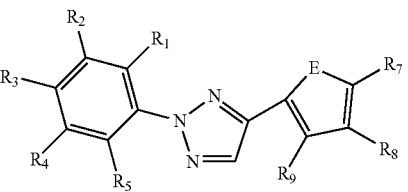
Formula Id wherein $R_1$ and $R_5$ are independently selected from the group consisting of hydrogen, $CH_3$, F, Cl, Br, $CF_3$, and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_7$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl;

with the proviso that when E is S and $R_1$, $R_2$, $R_4$, $R_5$, and $R_7$ through $R_9$ are each hydrogen, $R_3$ is other than F.

4. The compound of claim 1 wherein the compound is of Formula Ic or a salt thereof,

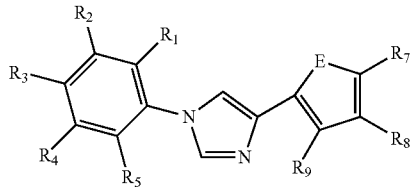
Formula Ic wherein $R_1$ and $R_5$ are independently selected from the group consisting of hydrogen, $CH_3$, F, Cl, Br, $CF_3$, and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_7$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl.

5. The compound of claim 1 wherein the compound is of Formula Id or a salt thereof, wherein $R_1$ and $R_5$ are independently selected from the group consisting of hydrogen, $CH_3$, F, Cl, Br, $CF_3$, and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_7$, $R_8$ and $R_9$ are independently selected from the group consisting of hydrogen, F, Cl, Br, $CH_3$, and $OCF_3$; and E is selected from the group consisting of O, S, and N—$R_{10}$, wherein $R_{10}$ is alkyl;

with the proviso that when E is O or S, at least one of $R_1$ through $R_5$ and $R_7$ through $R_9$ is other than hydrogen.

6. The compound of claim 2 wherein the compound of Formula Ia is selected from the group consisting of:
4-(furan-2-yl)-1-phenyl-1H-1,2,3-triazole, or a salt thereof;
1-(2,4-difluorophenyl)-4-(thiophen-2-yl)-1H-1,2,3-triazole, or a salt thereof;
1-(4-chlorophenyl)-4-(furan-2-yl)-1H-1,2,3-triazole, or a salt thereof;
1-(4-fluorophenyl)-4-(furan-2-yl)-1H-1,2,3-triazole, or a salt thereof;
1-(2,4-difluorophenyl)-4-(furan-2-yl)-1H-1,2,3-triazole, or a salt thereof; and
1-(4-chlorophenyl)-4-(thiophen-2-yl)-1H-1,2,3-triazole, or a salt thereof.

7. The compound of claim 3 wherein the compound of Formula Ib is selected from the group consisting of:
1-phenyl-4-(thiophen-2-yl)-1H-pyrazole, or a salt thereof;
1-(4-chlorophenyl)-4-(thiophen-2-yl)-1H-pyrazole, or a salt thereof; and
4-(furan-2-yl)-1-phenyl-1H-pyrazole, or a salt thereof.

8. The compound of claim 4 wherein the compound of Formula Ic is selected from the group consisting of:
1-(4-chlorophenyl)-4-(furan-2-yl)-1H-imidazole, or a salt thereof;
1-(4-chlorophenyl)-4-(thiophen-2-yl)-1H-imidazole, or a salt thereof; and
4-(furan-2-yl)-1-phenyl-1H-imidazole, or a salt thereof.

* * * * *